(12) United States Patent
Laufer et al.

(10) Patent No.: US 6,613,045 B1
(45) Date of Patent: Sep. 2, 2003

(54) METHOD AND APPARATUS FOR TREATING VENOUS INSUFFICIENCY

(75) Inventors: Michael D. Laufer, Menlo Park, CA (US); Brian E. Farley, Los Altos, CA (US); Grace Y. Schulz, San Carlos, CA (US); Arthur W. Zikorus, San Jose, CA (US); Mark P. Parker, San Jose, CA (US)

(73) Assignee: VNUS Medical Technologies, Inc., San Jose, CA (US)

( * ) Notice: Subject to any disclaimer, the term of this patent is extended or adjusted under 35 U.S.C. 154(b) by 0 days.

(21) Appl. No.: 09/495,667

(22) Filed: Feb. 1, 2000

Related U.S. Application Data

(63) Continuation of application No. 08/610,911, filed on Mar. 5, 1996, now Pat. No. 6,036,687.

(51) Int. Cl.$^7$ .............................................. A61B 18/04
(52) U.S. Cl. ........................ 606/27; 604/20; 604/113; 606/32
(58) Field of Search .................. 604/104–107, 604/19–21, 93.01, 113, 114; 606/27, 40, 32, 28, 41–50, 34; 128/642, 639; 607/1, 2, 96, 101, 103, 122, 113, 124, 126; 600/9, 11, 373, 372, 375, 374

(56) References Cited

U.S. PATENT DOCUMENTS

| | | |
|---|---|---|
| 373,339 A | 11/1887 | Hamilton |
| 659,409 A | 10/1900 | Mosher |
| 833,759 A | 10/1906 | Sourwine |
| 985,865 A | 3/1911 | Turner, Jr. |
| 3,230,957 A | 1/1966 | Seifert |
| 3,301,258 A | 1/1967 | Werner et al. |
| 3,557,794 A | 1/1971 | Van Patten |
| 3,920,021 A | 11/1975 | Hiltebrandt |

(List continued on next page.)

FOREIGN PATENT DOCUMENTS

| | | |
|---|---|---|
| DE | 3516830 | 11/1986 |
| EP | 0 189 329 A2 | 7/1986 |
| EP | 0 205 851 | 12/1986 |
| EP | 0 472 368 A2 | 2/1992 |
| EP | 0 629 382 A1 | 12/1994 |
| EP | 0 738 501 A1 | 10/1996 |

(List continued on next page.)

OTHER PUBLICATIONS

Aaron et al., *Electrofulguration for Varicose Veins*, The Medical Letter on Drugs and Therapeutics, Jul. 12, 1968, vol. 10, No. 14, Issue 248, p. 54.

Brunelle et al., *A Bipolar Electrode for Vascular Electrocoagulation with Alternating Current*, Technical Notes, Oct. 1980, vol. 137, pp. 239–240.

Cragg et al., *Endovascular Diathermic Vessel Occlusion*, Diagnostic Radiology, 144: 303–308, Jul. 1982.

(List continued on next page.)

*Primary Examiner*—Brian L. Casler
*Assistant Examiner*—Cris L. Rodriguez
(74) *Attorney, Agent, or Firm*—Fulwider Patton Lee & Utecht, LLP

(57) ABSTRACT

A catheter delivers an electrode within a vein for a minimally invasive treatment of varicose veins and venous insufficiency using RF energy. The catheter is introduced into a patient and positioned within the section of the vein to be treated. The electrode radiates high frequency energy towards the vein, and the surrounding venous tissue becomes heated and begins to shrink. The catheter includes a controllable member for limiting the amount of shrinkage of the vein to the diameter of the member. The electrode remains active until there has been sufficient shrinkage of the vein. The extent of shrinkage of the vein may be detected by fluoroscopy. After treating one section of the vein, the catheter and the electrode can be repositioned intraluminally within the vein to treat different sections of the vein until all desired venous sections and valves are repaired and rendered functionally competent.

28 Claims, 10 Drawing Sheets

U.S. PATENT DOCUMENTS

| | | | |
|---|---|---|---|
| 4,016,886 A | 4/1977 | Doss et al. | |
| 4,043,338 A | 8/1977 | Homm et al. | |
| 4,119,102 A | 10/1978 | LeVeen | |
| 4,154,246 A | 5/1979 | LeVeen | |
| 4,312,364 A | 1/1982 | Convert et al. | |
| 4,346,715 A | 8/1982 | Gammell | |
| 4,522,205 A | 6/1985 | Taylor et al. | |
| 4,643,186 A | 2/1987 | Rosen et al. | |
| 4,658,836 A | 4/1987 | Turner | |
| 4,660,571 A | 4/1987 | Hess et al. | |
| 4,664,120 A | 5/1987 | Hess | |
| 4,699,147 A | 10/1987 | Chilson et al. | |
| 4,709,698 A | 12/1987 | Johnston et al. | |
| 4,765,331 A | 8/1988 | Petruzzi et al. | |
| 4,776,349 A | 10/1988 | Nashef et al. | |
| 4,807,620 A | 2/1989 | Strul et al. | |
| 4,823,812 A | 4/1989 | Eshel et al. | |
| 4,945,912 A | 8/1990 | Langberg | |
| 4,966,597 A | 10/1990 | Cosman | |
| 4,976,711 A | 12/1990 | Parins et al. | |
| 4,979,948 A | 12/1990 | Geddes et al. | |
| 5,010,894 A | 4/1991 | Edhag | |
| 5,035,694 A | 7/1991 | Kasprzyk | |
| 5,057,106 A | 10/1991 | Kasevich et al. | |
| 5,057,107 A | 10/1991 | Parins et al. | |
| 5,078,717 A | 1/1992 | Parins et al. | |
| 5,098,429 A | 3/1992 | Sterzer | |
| 5,098,431 A | 3/1992 | Rydell | |
| 5,117,828 A | 6/1992 | Metzger et al. | |
| 5,122,137 A | 6/1992 | Lennox | |
| 5,156,151 A | 10/1992 | Imran | |
| 5,188,602 A | 2/1993 | Nichols | |
| 5,190,517 A | 3/1993 | Zieve et al. | |
| 5,215,103 A | 6/1993 | Desai | |
| 5,255,678 A | 10/1993 | Deslauriers et al. | |
| 5,263,493 A | 11/1993 | Avitall | |
| 5,275,610 A | 1/1994 | Eberbach | |
| 5,281,218 A | 1/1994 | Imran | |
| 5,293,869 A | 3/1994 | Edwards et al. | |
| 5,314,466 A | 5/1994 | Stern et al. | |
| 5,345,936 A * | 9/1994 | Pomeranz et al. | 600/374 |
| 5,370,677 A | 12/1994 | Rudie et al. | |
| 5,370,678 A | 12/1994 | Edwards et al. | |
| 5,383,917 A | 1/1995 | Desai et al. | |
| 5,397,339 A | 3/1995 | Desai | |
| 5,403,312 A | 4/1995 | Yates et al. | |
| 5,405,322 A | 4/1995 | Lennox et al. | |
| 5,405,346 A | 4/1995 | Grundy et al. | |
| 5,409,000 A | 4/1995 | Imran | |
| 5,411,025 A | 5/1995 | Webster, Jr. | |
| 5,423,815 A | 6/1995 | Fugo | |
| 5,431,649 A | 7/1995 | Mulier et al. | |
| 5,437,664 A | 8/1995 | Cohen et al. | |
| 5,447,529 A | 9/1995 | Marchlinski et al. | |
| 5,449,381 A | 9/1995 | Imran | |
| 5,454,809 A | 10/1995 | Janssen | |
| 5,458,596 A | 10/1995 | Lax et al. | |
| 5,462,545 A | 10/1995 | Wang et al. | |
| 5,465,717 A | 11/1995 | Imran et al. | |
| 5,472,441 A | 12/1995 | Edwards et al. | |
| 5,505,730 A | 4/1996 | Edwards | |
| 5,514,130 A | 5/1996 | Baker | |
| 5,545,161 A | 8/1996 | Imran | |
| 5,556,396 A | 9/1996 | Cohen et al. | |
| 5,626,578 A | 5/1997 | Tihon | |
| 5,643,257 A | 7/1997 | Cohen et al. | |
| 5,647,870 A | 7/1997 | Kordis et al. | |
| 5,709,224 A | 1/1998 | Behl et al. | |
| 5,810,804 A | 9/1998 | Gough et al. | |
| 5,817,092 A | 10/1998 | Behl | |
| 5,827,268 A | 10/1998 | Laufer | |
| 5,829,447 A * | 11/1998 | Stevens et al. | 128/898 |
| 5,863,290 A | 1/1999 | Gough et al. | |
| 5,868,740 A | 2/1999 | LeVeen et al. | |
| 5,916,193 A * | 6/1999 | Stevens et al. | 604/28 |
| 6,029,671 A * | 2/2000 | Stevens et al. | 128/898 |
| 6,240,307 B1 * | 5/2001 | Beatty et al. | 600/374 |

FOREIGN PATENT DOCUMENTS

| | | |
|---|---|---|
| WO | WO 90/07303 | 7/1990 |
| WO | WO 92/12681 | 8/1992 |
| WO | WO 93/21846 | 11/1993 |
| WO | WO 94/07446 | 4/1994 |
| WO | WO 94/21170 | 9/1994 |
| WO | WO 95/02370 | 1/1995 |
| WO | WO 95/10236 | 4/1995 |
| WO | WO 95/10322 | 4/1995 |
| WO | WO 95/10978 | 4/1995 |
| WO | WO 95/31142 | 11/1995 |
| WO | WO 96/32885 | 10/1996 |
| WO | WO 97/17892 | 5/1997 |

OTHER PUBLICATIONS

Crockett et al., *Preliminary Experience with an Endovascular Catheter for Electrocoagulation of Peripheral Veins*, The Journal of Vascular Technology, Winter 1996, at 19–22.

Gradman, *Venoscopic Obliteration of Variceal Tributaries Using Monopolar Electrocautery*, Journal of Dermatology Surgery Oncology, 1994, p. 482–485.

Inturri, *Pathophysiology of Portal Hypertension*, Journal of Vascular Technology 271–276, Sep.–Dec. 1995.

Money, *Endovascular Electroablation of Peripheral Veins*, 22nd Annual Symposium, Current Critical Problems, New Horizons and Techniques in Vascular and Endovascular Surgery (Nov. 1995).

Ogawa et al., *Electrothrombosis As a Treatment of Cirsoid Angioma in the Face and Scalp and Varicosis of the Leg*, Plastic and Reconstructive Surgery, No. 3, Sep. 1982, pp. 310–311.

O'Reilly, *Endovenous Diathermy Sclerosis as a Unit of the Armamentarium for the Attack on Varicose Veins*, The Medical Jourrnal of Australia, Jun. 1, 1974, at 900.

O'Reilly, *Endovenous Diathermy Sclerosis of Varicose Veins*, The Australia, New Zealand Journal of Surgery, vol. 47, No. 3, Jun. 1977, pp. 393–395.

O'Reilly, *A Technique of Diathermy Sclerosis of Varicose Veins*, The Australia, New Zealand Journal of Surgery, vol. 51, No. 4, Aug. 1981, pp. 379–382.

Watts, G.T., *Endovenous Diathermy Destruction of Internal Saphenous*, British Medical Journal, Oct. 7, 1972, p. 53.

* cited by examiner

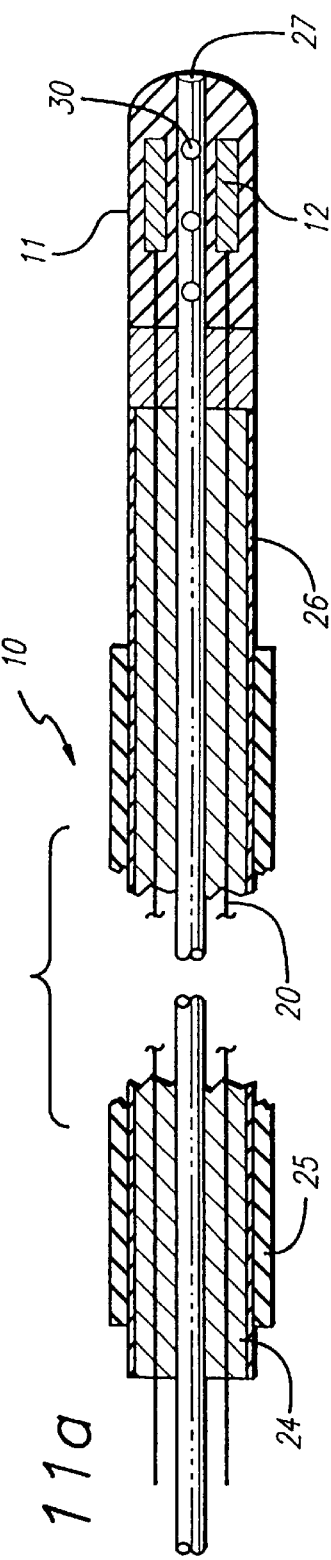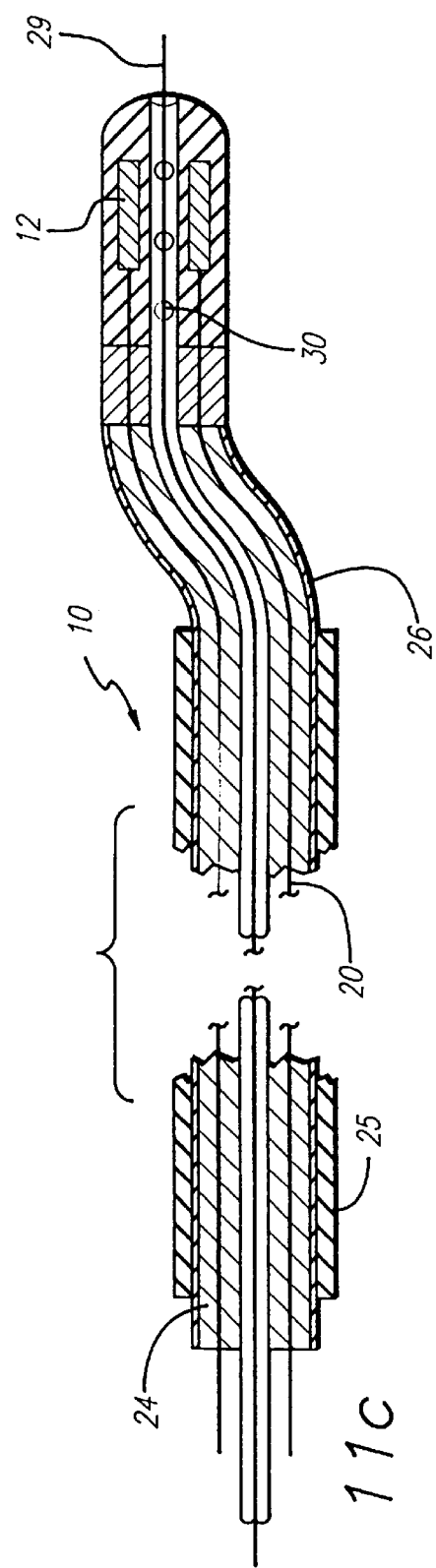
FIG. 11a
FIG. 11b
FIG. 11c

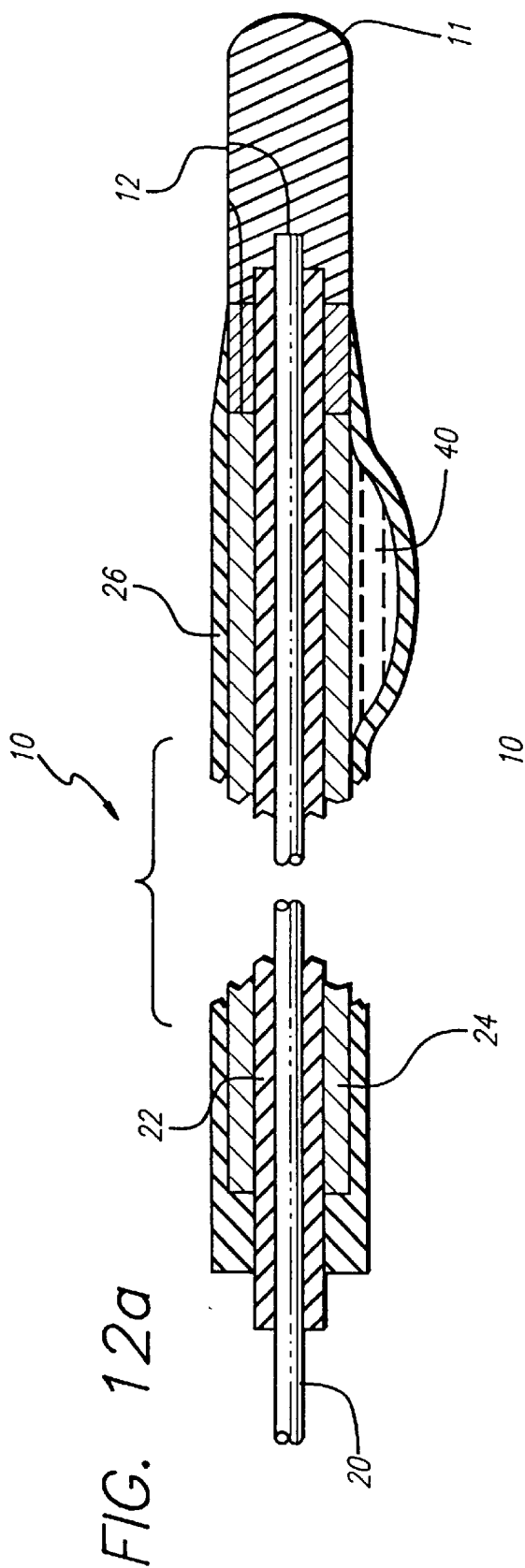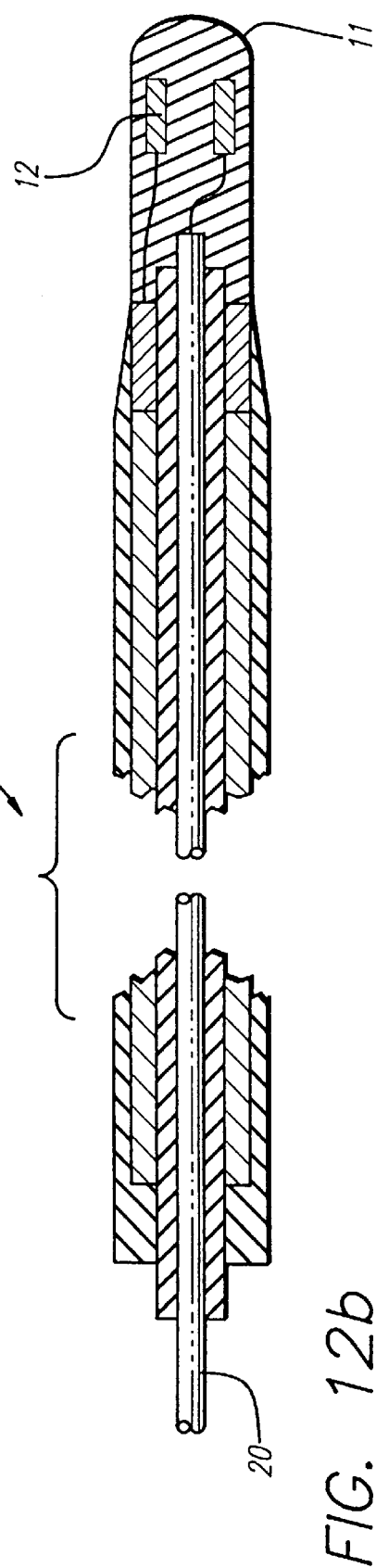

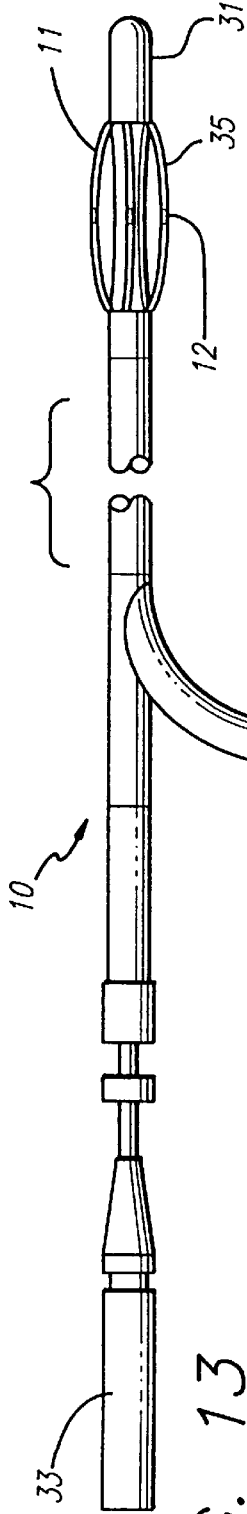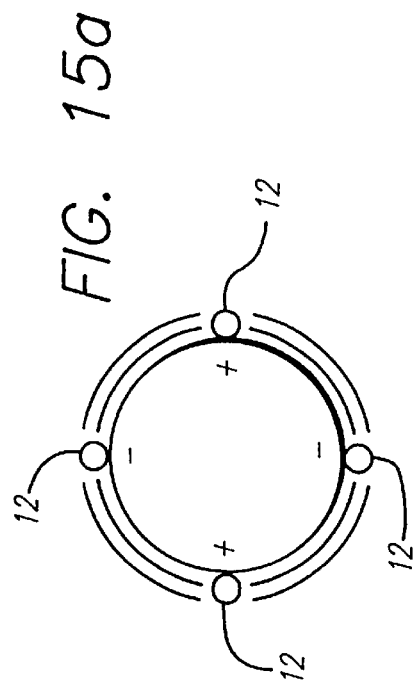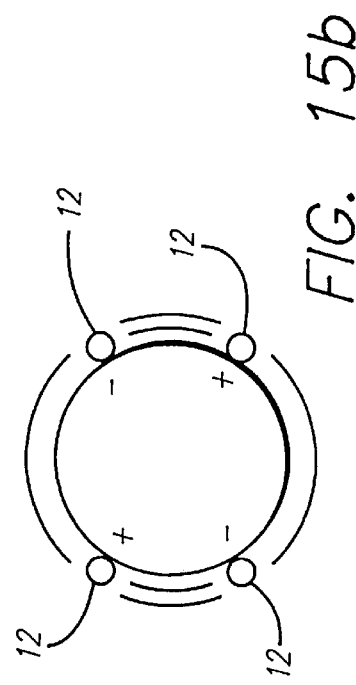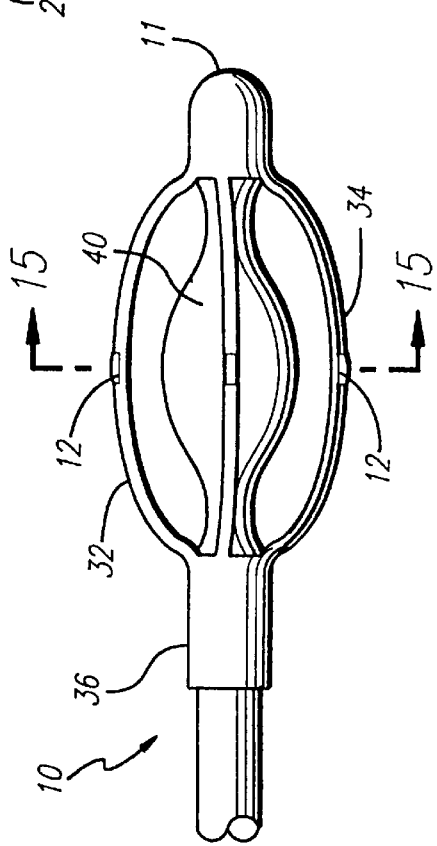
FIG. 13
FIG. 15a
FIG. 15b
FIG. 14

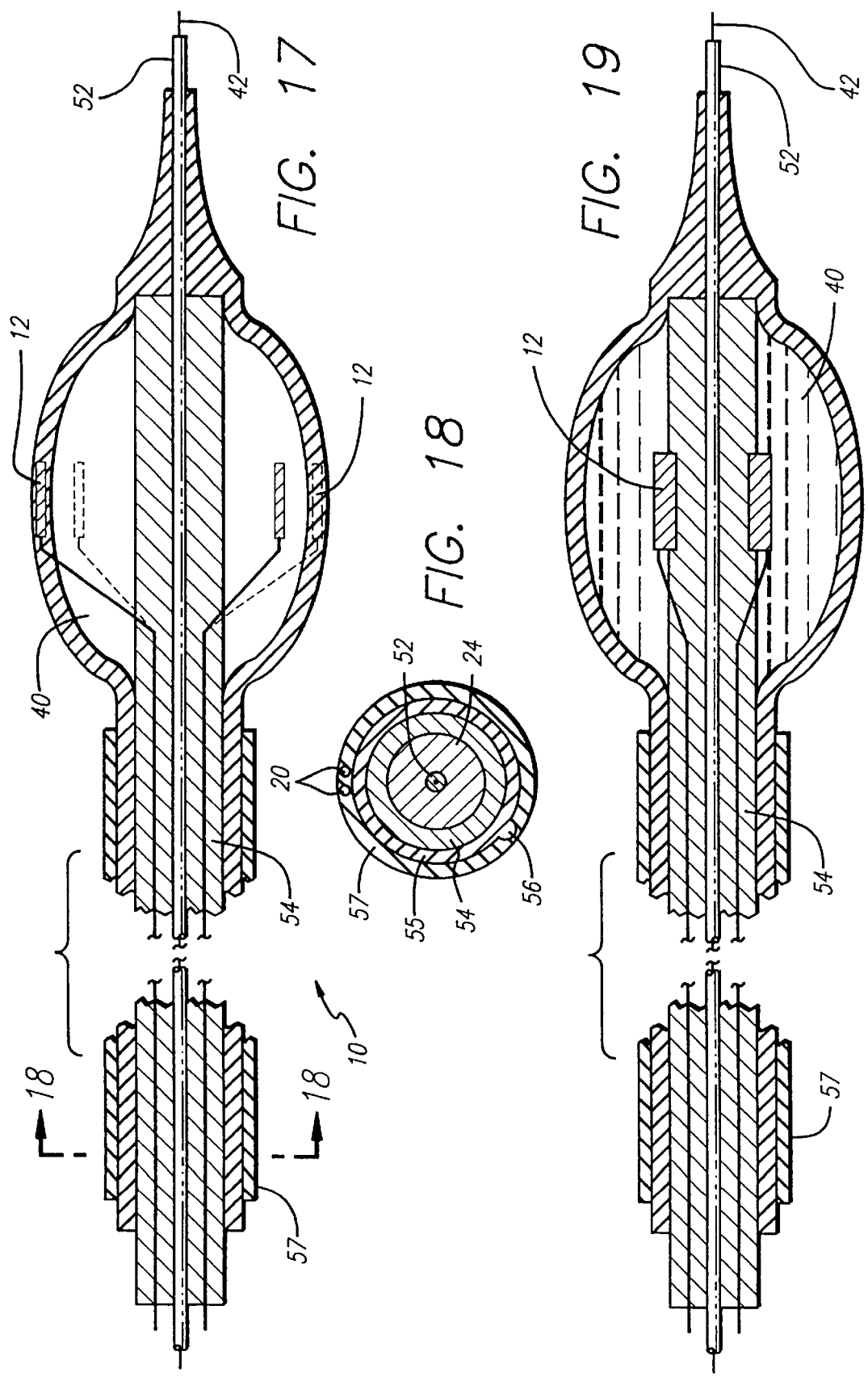

METHOD AND APPARATUS FOR TREATING VENOUS INSUFFICIENCY

This is a continuation of application Ser. No. 08/610,911, filed Mar. 5, 1996, now U.S. Pat. No. 6,036,687.

BACKGROUND OF THE INVENTION

This invention relates to the treatment and correction of venous insufficiency or varicose veins, and more particularly to a minimally invasive procedure using a catheter-based system to deploy an electrode for providing radio frequency (RF) energy, microwave energy, or thermal energy to shrink a vein intraluminally to change the fluid flow dynamics and to restore the competency of the venous valve and the proper function of the vein.

The human venous system of the lower limb consists essentially of the superficial venous system and the deep venous system with perforating veins connecting the two systems. The superficial system includes the long or great saphenous vein and the short saphenous vein. The deep venous system includes the anterior and posterior tibial veins which unite to form the popliteal vein, which in turn becomes the femoral vein when joined by the short saphenous vein.

The venous systems contain numerous one-way valves for directing blood flow back to the heart. Venous valves are usually bicuspid valves, with each cusp forming a sack or reservoir for blood which, under pressure, forces the free surfaces of the cusps together to prevent retrograde flow of the blood and allow antegrade flow to the heart. When an incompetent valve is in the flow path of retrograde flow toward the foot, the valve is unable to close because the cusps do not form a proper seal and retrograde flow of blood cannot be stopped.

Incompetence in the venous system can result from vein dilation, which causes the veins to swell with additional blood. Separation of the cusps of the venous valve at the commissure may occur as a result. The leaflets are stretched by the dilation of the vein and concomitant increase in the vein diameter which the leaflets traverse. Stretching of the leaflets of the venous valve results in redundancy which allows the leaflets to fold on themselves and leave the valve open. This is called prolapse, which can allow reflux of blood in the vein. Eventually the venous valve fails, thereby increasing the strain and pressure on the lower venous sections and overlying tissues. Two venous diseases which often involve vein dilation are varicose veins and chronic venous insufficiency.

The varicose vein condition includes dilatation and tortuosity of the superficial veins of the lower limb, resulting in unsightly discoloration, pain and ulceration. Varicose veins often involve incompetence of one or more venous valves, which allow reflux of blood from the deep venous system to the superficial venous system or reflux within the superficial system. Current treatments include such invasive open surgical procedures as vein stripping, sclerotherapy, and occasionally, vein grafting, venous valvuloplasty, and the implantation of various prosthetic devices. The removal of varicose veins from the body can be a tedious, time-consuming procedure having a painful and slow healing process. Complications, scarring, and the loss of the vein for future cardiac and other by-pass procedures may also result. Along with the complications and risks of invasive open surgery, varicose veins may persist or reoccur, particularly when the valvular problem is not corrected. Due to the long, arduous, and tedious nature of the surgical procedure, treating multiple venous sections can exceed the physical stamina of the physician, and thus render complete treatment of the varicose vein conditions impractical.

Chronic venous insufficiency (CVI) is a problem caused by hydrodynamic forces acting on the tissues of the body, especially the legs, ankles and feet. As the veins dilate due to increased pressure, the valves in the veins fail. This causes the pressure to increase on the next valve and vein segment down, causing those veins to dilate, and as this continues, the valves in the veins eventually all fail. As they fail, the effective height of the column of blood above the feet and ankles grows, and the weight and hydrostatic pressure exerted on the tissues of the ankle and foot increases. When the weight of that column reaches a critical point from the valve failures, ulcerations of the ankle begin to form, which start deep and eventually come to the surface. These ulcerations do not heal easily because the weight of blood which caused them continues to persist, and have the tendency to enlarge the ulcer.

Chronic venous insufficiency often consists of hypertension of the lower limb in the deep, perforating and often superficial veins, and may result in discoloration, pain, swelling and ulceration. Existing treatments for chronic venous insufficiency are often less than ideal. These treatments include the elevation of the legs, compressing the veins externally with elastic support hose, and surgical repair by grafting vein sections with healthy valves from the arm into the leg. These methods have variable effectiveness. Moreover, invasive surgery has its associated complications with risk to life and expense. Similarly, the palliative therapies require major lifestyle changes for the patient. For example, the ulcers will reoccur unless the patient continues to elevate the legs and use support hose continuously throughout the life of the patient.

Due to the time-consuming and invasive nature of the current surgical treatments, such as vein grafting, typically only one valve is treated during any single procedure. This greatly limits the ability of the physician to fully treat patients suffering from chronic venous insufficiency. Every instance of invasive surgery, however, has its associated complications with risk to life and expense.

The ligation of vascular lumen by tying a suture around them, cauterization or coagulation using electrical energy from an electrode has been employed as an alternative to stripping, or the surgical removal of such veins. However, ligation procedures close off the lumen, essentially destroying their functional capability. For example, it is known to introduce an electrode into the leg of a patient, and position the electrode adjacent to the exterior of the varicose veins to be treated. Through a small stab incision, a probe is forced through the subcutaneous layer between the fascia and the skin, and then to the various veins to be destroyed. Electrodes at the outer end of the probe are placed adjacent to the varicose veins. Once properly positioned, an alternating current of 500 kilohertz is applied to destroy the adjacent varicose veins by fulguration. The fulgurated veins lose the function of allowing blood to flow through, and are no longer of use. For example, ligating the saphenous vein would render that vein unavailable for harvesting in other surgical procedures such as coronary by-pass operations. Ligation techniques which functionally destroy the vein lumen would appear to be inappropriate to a corrective procedure for restoring and maintaining the function of the vein.

A need exists in the art to treat dilated veins, such as those resulting in varicose veins or from venous insufficiency, which maintains the patency of the veins for venous function and yet restores valvular competency.

SUMMARY OF THE INVENTION

Briefly, and in general terms, the present invention provides a less invasive and faster method for solving the underlying problems of varicose veins and venous insufficiency, and uses a novel repair system, including a catheter for placement of an electrode for delivering radio frequency energy. The present invention includes a method of applying energy to cause shrinkage of a vein, the method comprising the steps of introducing a catheter having a working end and means for heating located at the working end, to a treatment site in a vein; positioning the means for heating at the treatment site in the vein; applying energy from the means for heating to controllably heat the treatment site and cause shrinkage of the vein; and terminating the emission of energy from the means for heating after sufficient shrinkage of the vein has occurred so as to restore valvular competency or so that the vein remains patent so as to continue to function as a blood conduit.

The method of the present invention is a minimally invasive procedure which eliminates the need for open surgical procedures for venous repair, including venous valvuloplasty, and the transplantation of an arm vein into the leg.

An apparatus for performing the method of applying radiant energy to cause shrinkage of a vein, comprises a catheter having a working end, means for heating a venous treatment area to cause shrinkage of the vein, wherein the means for heating is located at the working end of the catheter, and means for preventing further shrinkage after sufficient shrinkage of the vein, so that the vein continues to function. The heating means may include RF electrodes to heat and shrink the vein. Balloons, or other mechanisms for controlling the outer diameter of the heating means, may be used to limit the amount of shrinkage. Feedback control systems may be applied to these mechanisms, or may be used to control the application of energy to heat the venous tissue, in order to control the amount of shrinkage.

Features of the present invention include restoring the competence of venous valves, normalizing flow patterns, dynamics, and pressure, and reducing sections of dilated varicose veins to a normal diameter for cosmetic purposes. The treated veins remain patent and can continue to function and return blood to the heart.

One feature of the present invention is to provide a procedure for restoring venous valvular competency by controllably shrinking the otherwise dilated lumen of the vein to a desired diameter.

Another feature of the present invention is to control or adjust the effective diameter of the catheter or electrode configuration in order to control the amount of circumferential shrinking experienced by the vein wall. An extendable member located adjacent to the working end of the catheter can increase the effective diameter of the catheter and limit the shrinkage of the vein.

Another feature of the present invention is to provide a catheter electrode which generates a radio frequency field around the circumference of the catheter in order to shrink the vein wall circumferentially and omnidirectionally while minimizing lengthwise contraction when the catheter electrode is positioned intraluminally within the vein.

Yet another feature of the present invention is to generate a field at a specific frequency around the catheter in order to minimize coagulation within the vein, and to control the spread of heating within the venous tissue.

An additional feature of the present invention is to protect the venous valve leaflets by minimizing the heating effect on the venous valves by the selective positioning of the electrodes within the vein.

Another feature of the present invention is to deliver cooling fluid to the bloodstream in order reduce the likelihood of heating the blood to a point of coagulation.

An additional feature of the present invention is to prevent shrinkage of the vein past the end of the catheter.

Another feature of the present invention is to maintain the electrodes in apposition to the venous tissue to ensure that the heat is delivered towards the venous tissue, and not the blood moving through the vein.

Another feature of the present invention is to use electrodes which are bowable members that can be deflected radially outward for maintaining contact with the venous tissue. The bowable members are conductive longitudinal electrodes substantially covered by an insulating film, except for the portion which is to come into apposition with the venous tissue.

Another feature of the present invention is a balloon located on one side of the catheter having electrodes on the opposite side. Inflation of the balloon will move the electrodes into apposition with the vein wall on the opposite side.

Yet another feature of the present invention is to provide a procedure which can treat multiple venous sites quickly and easily.

An additional feature of the present invention is that no foreign object or prothesis remain in the vasculature after treatment.

These and other aspects and advantages of the present invention will become apparent from the following more detailed description, when taken in conjunction with the accompanying drawings which illustrate, by way of example, the principles of the invention.

BRIEF DESCRIPTION OF THE DRAWINGS

FIGS. 11a, 11b, and 11c show partial cross-sectional views of another embodiment of the catheter having a bendable tip which deflects laterally for causing apposition between the electrodes of the catheter and the vein wall in accordance with the invention;

FIGS. 12a and 12b show partial cross-sectional side and top views, respectively, of another embodiment of the catheter having a balloon on one side of the catheter and longitudinal electrodes on the other side at the working end of the catheter for moving the electrodes into appositional contact with the vein wall in accordance with the invention;

FIG. 13 shows another embodiment of the catheter having bendable electrodes which deflect outwardly for increasing the effective diameter at the working end of the catheter in accordance with the invention;

FIG. 14 shows another embodiment of the catheter having a balloon and bendable members with electrodes which deflect outwardly for increasing the effective diameter at the working end of the catheter in accordance with the invention;

FIG. 15a shows a cross-sectional view of an embodiment of the catheter shown in FIG. 14 having four equidistantly spaced electrodes in accordance with the present invention;

FIG. 15b shows a cross-sectional view of an embodiment of the catheter shown in FIG. 14 having four electrodes preferentially spaced to form two pairs of electrodes in accordance with the present invention;

FIG. 17 shows a partial cross-sectional view of an embodiment of an over-the-wire balloon catheter having four equidistantly spaced apart electrodes on the surface of the balloon in accordance with the present invention;

FIG. 18 shows a cross-sectional view taken along the lines 18—18 of the over-the-wire balloon catheter of FIG. 17 in accordance with the present invention;

FIG. 19 shows a partial cross-sectional view of another embodiment of the catheter having electrodes located within the balloon portion in accordance with the present invention;

DETAILED DESCRIPTION OF PREFERRED EMBODIMENTS

Figure 1:
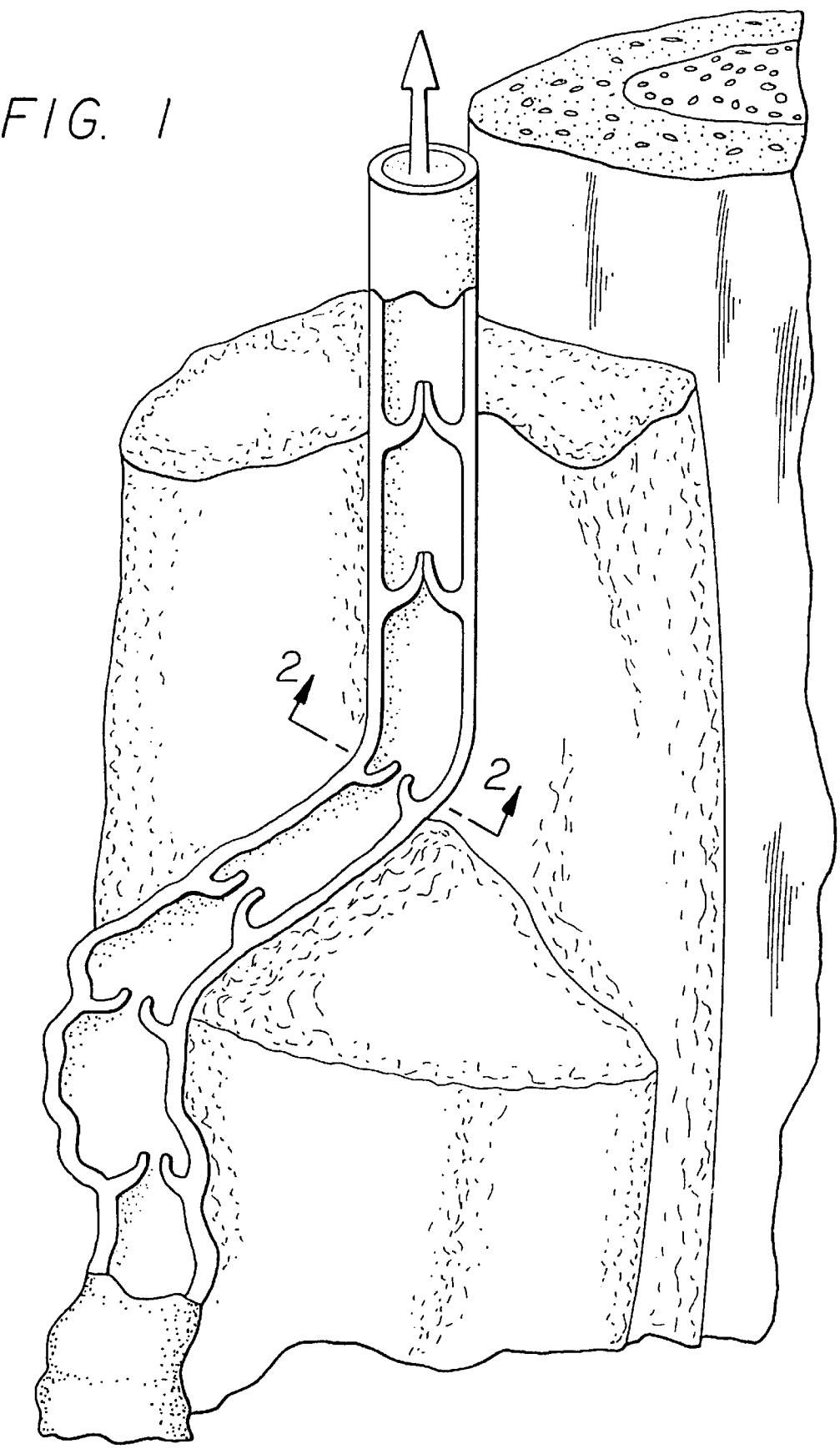
FIG. 1 shows a cross-sectional view of a dilated vein having incompetent venous valves in a lower limb which are to be treated in accordance with the present invention.

As shown in the exemplary drawings, the invention is directed toward the intravenous treatment of veins using a catheter to deliver at least one electrode to a venous treatment site. As used herein, like reference numerals will designate similar elements in the various embodiments of the present invention to be discussed. In addition, unless otherwise noted, the term working end will refer to the direction toward the treatment site in the patient, and the term connecting end will refer to the direction away from the treatment site in the patient. The invention will be described in relation to the treatment of the venous system of the lower limbs. It is to be understood, however, that the invention is not limited thereto and may be employed intraluminally to treat veins in other areas of the body such as hemorrhoids, esophageal varices, and venous-drainage-impotence of the penis. Furthermore, although the invention will be described as using RF energy from the electrode, it is to be understood that other forms of energy such as microwaves, ultrasound, direct current, circulating heated fluid, radiant light, and lasers can be used, and that the thermal energy generated from a resistive coil or curie point element may be used as well.

A partial cross-sectional view of a dilated vein from a lower limb having incompetent valves is shown in FIG. 1. These veins are often disposed within muscle tissue. Veins have bicuspid valves, and in a normal and competent valve, each cusp forms a sack or reservoir for blood which, under pressure, forces the free edges of the cusps together to prevent retrograde flow of the blood and allow only antegrade flow to the heart. The arrow leading out the top of the vein represents the antegrade flow of blood back to the heart. The venous valves prevent retrograde flow as blood is pushed forward through the vein lumen and back to the heart.

Figure 2:
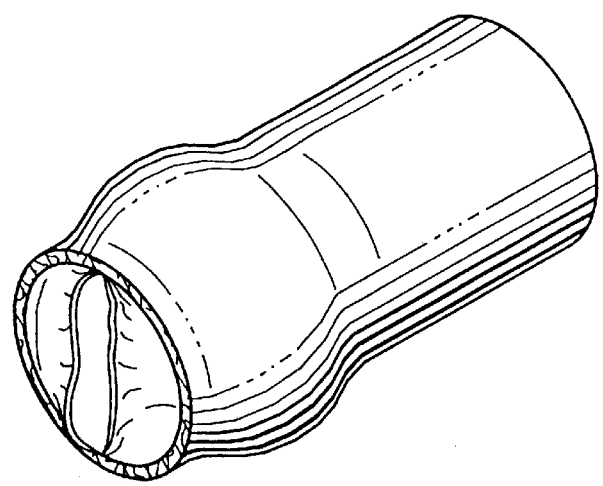
FIG. 2 shows a representative view of a venous section from FIG. 1 taken along lines 2—2 which is to be treated in accordance with the present invention.

When an incompetent valve encounters retrograde flow, the valve is unable to close, the cusps do not seal properly and retrograde flow of blood may occur. Incompetent valves may result from the stretching of dilated veins. As the valves fail, increased pressure is imposed on the lower veins and the lower valves of the vein, which in turn exacerbates the failure of these lower valves. A cross-sectional perspective view of a dilated vein taken along lines 2—2 of FIG. 1 is illustrated in FIG. 2. The valve cusps can experience some separation at the commissure due to the thinning and stretching of the vein wall at the cusps.

Figure 3:
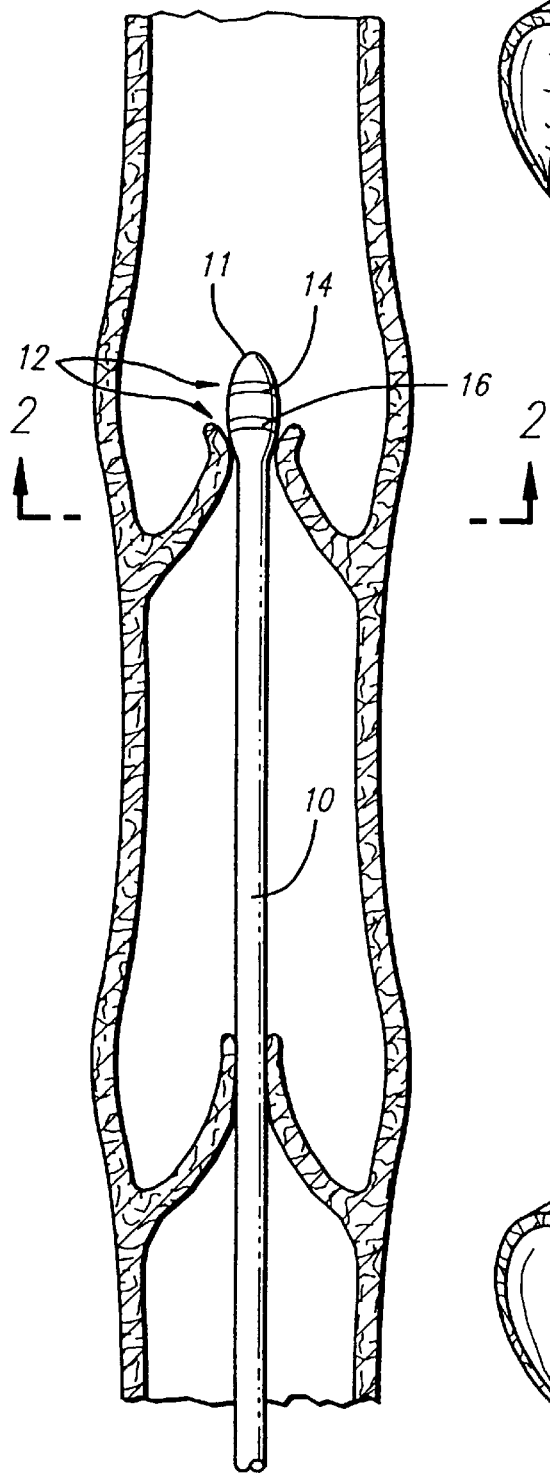
FIG. 3 shows a partial cross-sectional view of a catheter having electrodes being delivered antegrade to a venous treatment site in accordance with the present invention.

The method of the present invention for the minimally invasive treatment of venous insufficiency can be performed using a catheter 10 to deliver electrodes 12 to a venous treatment site in order to restore the competency of a vein. One embodiment of the catheter 10 for delivering the electrodes 12 to the venous treatment site is shown in FIG. 3. The electrodes 12 may be two RF ring electrodes 14 and 16 located at the working end 11 of the catheter 10. This and other embodiments of the catheter 10 will be described in greater detail later. Further, the method is contemplated to be used with any suitable appliance for applying radiant energy, thermal energy, or other forms of energy to heat and shrink the venous tissue in the repair or reconfiguration of incompetent veins in order to restore venous function or valvular competency. Particular discussion will be directed to the treatment of incompetent and varicose veins in the legs, although the method of the present invention is well suited to treating veins in other areas of the body.

When treating the veins of the lower limbs, the patient is typically placed onto a procedure table with the feet dependent in order to fill the veins of the leg. The leg of the patient is prepped with antiseptic solution. A percutaneous introducer is inserted into the vein using the well-known Seldinger technique to access the saphenous or deep vein system. Alternatively, a venous cut-down can be used to access the vein system to be treated. The procedure for the repair of incompetent veins can be accomplished by a qualified physician with or without fluoroscopic or ultrasonic observation, or under direct visualization. Further, the physician could palpate the treatment area to determine the location of the catheter, and the treatment site, during the procedure when treating the superficial venous system.

The catheter 10 could be passed within the vein after insertion through the introducer, and advanced through to the venous treatment site. Alternatively, a guide wire for the catheter may be inserted into the vein. The wire is advanced antegrade to the venous treatment site, such as the level of the most proximal incompetent vein site which is to be repaired. The catheter is then inserted upon the wire and is fed up the leg through the vein to the level of the venous section where retrograde flow exists. In either case, the catheter 10 delivers the electrodes 12 to the venous treatment site. Fluoroscopy, x-ray, ultrasound, or a similar imaging technique could then be used to direct the specific placement of the catheter and confirmation of position within the vein. X-ray contrast material can be injected through or around the catheter to identify the incompetent venous sections to be repaired.

From the antegrade approach, the catheter can be pushed through the venous valve so that the electrodes are positioned across the valve of the incompetent venous section to be treated. The catheter 10 travels antegrade through the venous valves, as shown in FIG. 3, and is positioned so that the electrodes 12 are near a dilated section of the vein to be treated. The electrodes may be positioned so as to extend past the incompetent venous valve. When the electrodes 12 of the catheter 10 are positioned at the venous treatment site, the RF generator is activated to provide suitable RF energy, preferably at a selected frequency from a range of 250 kHz to 350 MHZ. One suitable frequency is 40 Mhz. One criteria for the selection of the applied frequency is the minimization of coagulation in the vein. Another criteria is to control the spread and depth of the thermal effect in the tissue. The extent of heating or depth of penetration into the tissue generally increases with lower frequencies, and decreases as the frequency increases. A microprocessor can be used to select a frequency for treating different veins according to the above criteria. For example, the microprocessor can include a table stored in memory for associating specific frequencies for treating various veins and vein diameters according to the criteria of minimizing coagulation and controlling the spread or depth of the heating effect. The energy emitted from the electrodes is converted within the venous tissue into heat. As the temperature of the venous tissue increases, the venous tissue begins to shrink. The shrinkage is due in part to dehydration and the structural transfiguration of the collagen fibers in the vein. Although the collagen becomes compacted during this process, the collagen still retains some elasticity. When RF energy is applied near the locus of the dilated vein and venous valve, shrinkage of the vein can restore valvular competency by reducing the dilation which is preventing the proper functioning of the venous valve.

The working end 11 of the catheter 10 near the electrodes 12 physically limits the amount of shrinkage. The working end 11 is preferably sufficiently sized or enlarged to prevent the complete ligation of the vein. Other schemes, such as an inflatable balloon, may be used to mechanically limit or control the amount of shrinkage in the vein.

Vein dilation is reduced after RF energy applied from the electrodes 12 heats the surrounding venous tissue to cause shrinkage. RF energy is no longer applied after there has been sufficient shrinkage of the vein to alleviate the dilation of the vein near the valves, so as to restore venous function or valvular competency. Sufficient shrinkage may be detected by fluoroscopy, external ultrasound scanning, intravascular ultrasound scanning, impedance monitoring, temperature monitoring, direct visualization using an angioscope, or any other suitable method. For example, the catheter 10 can be configured to deliver x-ray contrast medium to allow visualization by fluoroscopy for assessing the condition of the vein and the relationship of the catheter to the treatment area of the vein during the shrinkage process. As an alternative to fluoroscopy, external ultrasound techniques such as B-scanning using distinct ultrasound signals from different angles, or intravascular ultrasound can be used to acquire a more multidimensional view of the vein shrinkage at the treatment site, which improves the detection of uneven shrinkage in the vein. An angioscope may also be used to directly visualize and determine the extent and degree of vein shrinkage.

Figure 4:
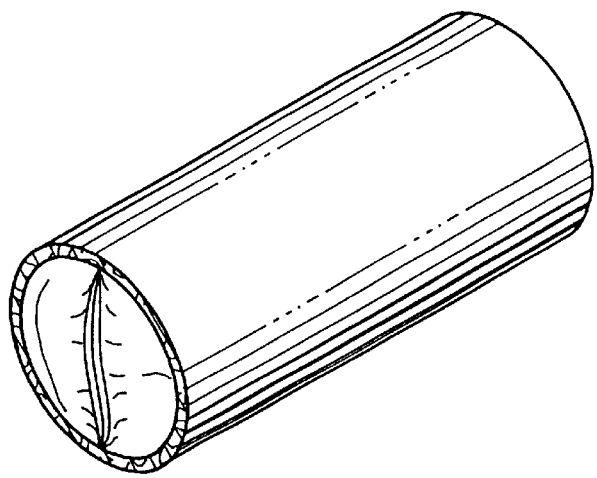
FIG. 4 shows the partial cross-sectional view of the venous section of FIG. 2 after being treated in accordance with the present invention.

After treatment, the commissure and the cusps of the venous valves should be closer together with little separation or prolapse, which indicates a restoration of the competency of the valve. A cross-sectional view of the venous valve after being treated with RF energy is shown in FIG. 4. Valvular competence may be determined by contrast injection or Doppler probe measurement.

Substantial shrinkage may be achieved very rapidly, depending upon the specific treatment conditions. Because the shrinkage can proceed at a rather rapid rate, the RF energy is preferably applied at low power levels. As previously discussed, the frequency of the RF energy is selected to minimize coagulation and to control the spread of the heating effect at the treatment site. The properties of the treatment site, such as temperature, can be monitored to provide feedback control for the RF energy in order to minimize coagulation. Other techniques such as impedance monitoring, and ultrasonic pulse echoing, can be utilized in an automated system which shuts down the application of RF energy from the electrodes to the venous section when sufficient shrinkage of the vein is detected and to avoid overheating or cauterization of the vein. Monitoring these values in an automatic feedback control system for the RF energy can also be used to control the spread, including the depth, of the heating effect. In all instances, the application of RF energy is controlled so as to shrink the venous tissue sufficiently to restore and maintain the competency of the venous valve.

Figure 5:
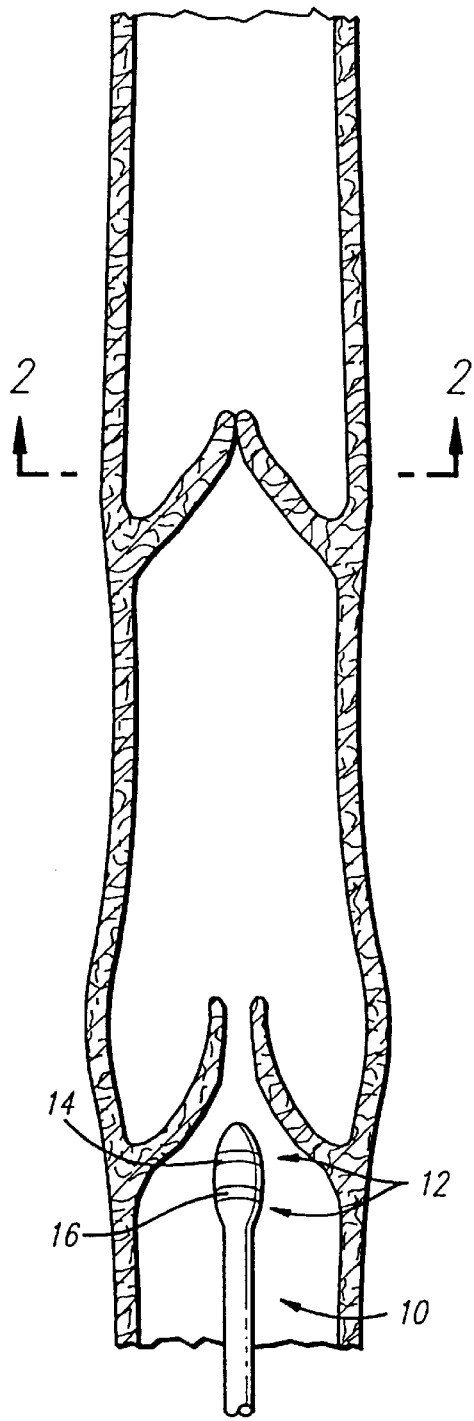
FIG. 5 shows a partial cross-sectional view of the catheter and vein shown in FIG. 3 being delivered to another venous treatment site in accordance with the present invention.

After treating the venous section shown in FIG. 3, the catheter 10 is moved to the next lower venous valve suffering from insufficiency as shown in FIG. 5. The electrode 12 may be placed across the venous valve as discussed previously in connection with FIG. 3. However, an alternative placement of the electrode 12 may be used. For example, as shown in FIG. 5, the electrode 12 is positioned just below or retrograde to the cusps of the venous valve. Placement of the electrode below the valve when applying RF energy can be advantageous in minimizing the effect of localized RF heating on the thin cusps of the venous valve while still achieving shrinkage of the vein to restore venous function or valve competency.

Where the catheter is designed with a fluid delivery lumen, a cooling fluid can be delivered through the delivery lumen to the bloodstream during RF heating of the vein being treated. The delivered cooling fluid minimizes any heating effect on the blood, and reduces the risk of heating the blood to the point of coagulation. The fluid may be delivered through ports formed along the side of the catheter near the working end and the electrodes.

While the method has thus far been described as restoring valvular competency, the invention is not so limited. A contiguous axial section of dilated vein can be treated by applying RF energy along the dilated venous section, even if the section is extensive. The dilated vein is shrunk and reduced to a normal diameter under the controlled application of RF energy in accordance with the present invention. Such treatment can be used in the cosmetic treatment of varicose veins. Further, thickening of the vein may occur during treatment, which can reduce the likelihood of the recurrence of varicose veins and venous insufficiency.

The catheter 10 can be repositioned to treat as many venous sections and valves as necessary. RF energy is applied to each venous section to be repaired, until all of the desired venous sections are repaired and the valves are rendered competent. Multiple incompetent valves and insufficient or dilated venous sections may be treated and repaired in a single minimally invasive procedure. If desired, a second introducer can be inserted into the limb of a patient in order to access either the deep or the superficial vein system, whichever has yet to be treated. The catheter can then be used to treat incompetent venous sections in the other vein system.

Instead of the antegrade approach, as shown in FIGS. 3 and 5, the catheter can deliver the electrodes to the venous treatment site from a retrograde direction. The catheter 10 is introduced through the skin and into the vein in a retrograde direction. The catheter 10 can penetrate the vein above and adjacent to the incompetent venous section to be treated. The electrodes are advanced until contact with the cusp of the venous valve is observed by fluoroscopy, ultrasound, or other detection method. The catheter is then pulled back slightly to allow treatment of the dilated section of vein. The electrodes are activated to deliver RF energy to the venous tissue and shrink the vein. The shrinkage of the vein can be limited to prevent ligation and allow the continued function of the vein. The outer diameter of the catheter or an extendable member can be controlled to limit the magnitude of the vein shrinkage.

More specific application of the RF energy to the separating commissures of venous valves can be effective in restoring venous function and valvular competency. The catheter 10 can be configured to position the electrodes within the vein and to appose the electrodes with the venous section to be repaired. The catheter is capable of being deflected, torqued, or otherwise moved to allow for proper placement of the electrode. Alternatively, a permanent bend may be formed near the working end of the catheter, which can then be turned and twisted in order to achieve the desired apposition. Manipulating the working end of the catheter enables preferential heating along the vein wall being treated, if desired, where the electrodes are placed closer to one side of the vein wall.

Figure 6:
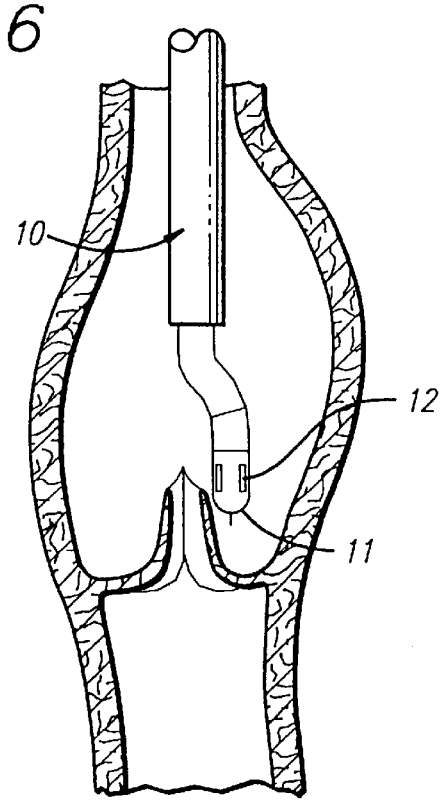
FIG. 6 shows a partial cross-sectional view of a catheter being delivered retrograde and deflected laterally to a venous treatment site in accordance with the present invention.

The electrodes 12 on a deflected catheter, as shown in FIG. 6, can be placed in close apposition to the vein walls near the commissure from a retrograde approach. The catheter may also be manipulated to place the electrodes in close apposition to the commissures of the venous valve to cause local shrinkage near the commissures to remedy any separation of the commissures from vein dilation and to restore venous function and valvular competency. After treating one end of the valvular commissure, the catheter may then be moved to place the electrodes near the commissure at the opposite end of the valve. Thus, after selectively applying RF energy to one side of the vein wall, the catheter can be turned 180 degrees around to apply energy to the other side of the vein wall, so as to promote the restoration of the function of the vein. Alternatively, an asymmetrical balloon as shown in FIG. 12, or another such positioning device, can be used to appose the electrodes against the venous section to be treated. The balloon may be deflated and then inflated to allow easier movement and repositioning of the catheter.

After treating one section of the vein, the catheter can be moved to the level of the next section of vein to be repaired. The same procedure would then be repeated for each subsequent instance of vein repair. The treatment may be repeated several times until sufficient shrinkage is achieved to restore venous function and valvular competence, while the vein retains patency. After completing the treatment for the incompetent venous sections, the electrode containing catheter is removed from the vein.

Figure 7:
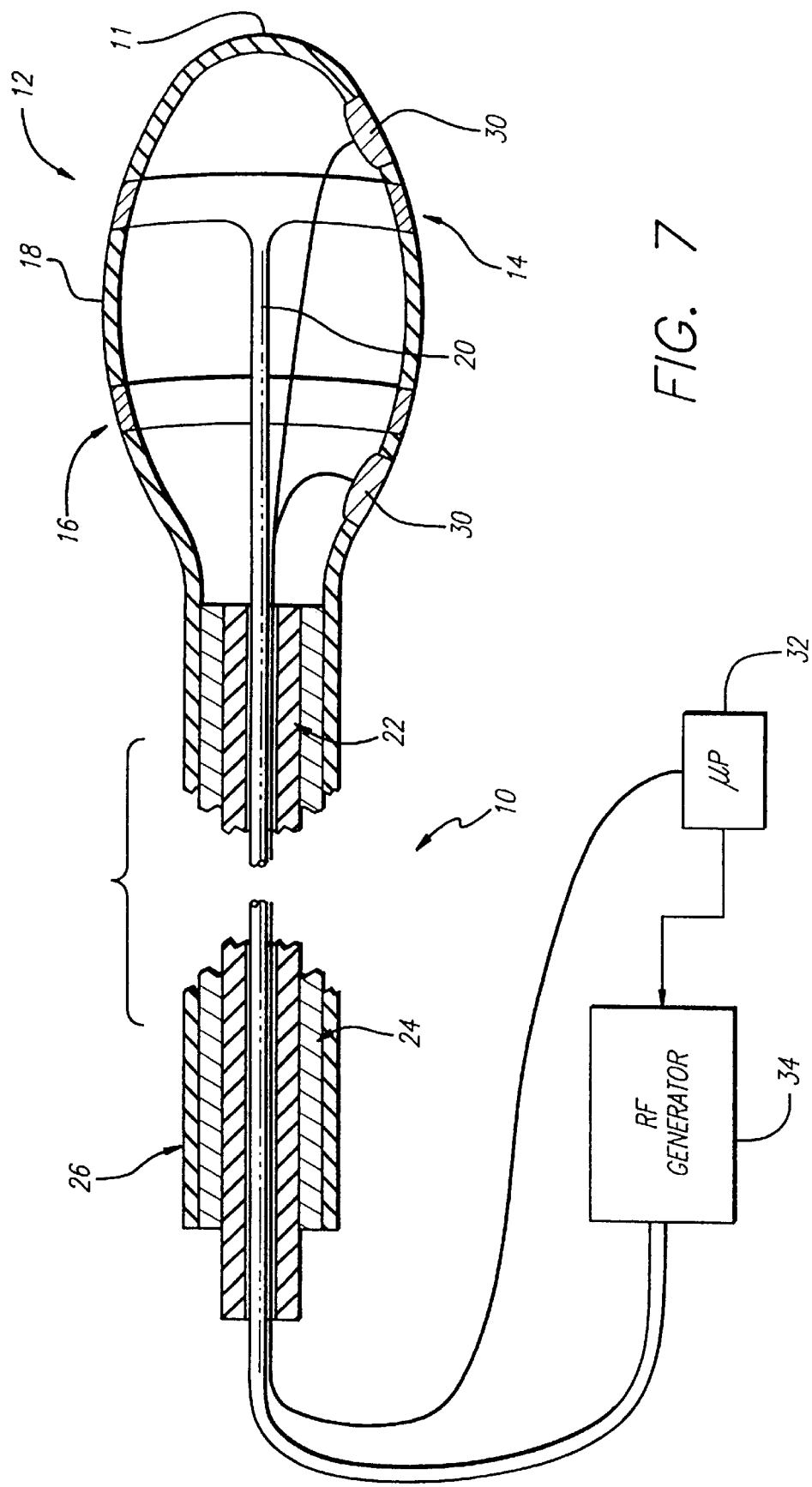
FIG. 7 shows a partial cross-sectional view of an embodiment of the catheter having a bulbous tip and ring electrodes for treating a dilated vein in accordance with the present invention.

An embodiment of the catheter 10 having electrodes 12 on the working end 11 which causes localized heating of the surrounding venous tissue and shrinkage of the vein described, as shown on FIGS. 3 and 5, is shown in more detail in FIG. 7. The electrodes 12 include two ring electrodes 14 and 16. The end ring electrode 14 can act as the active electrode, and the ring electrode 16 can act as the return electrode, or vice versa. The end ring electrode 14 is preferably spaced away from the tip of the working end of the catheter which may be formed from plastic or some other non-conductive material. The RF field created by the ring electrodes 14 and 16 should not extend past the end of the catheter. The inert non-conductive tip of the working end of the catheter helps prevent shrinkage past the end of the catheter by limiting the extent and formation of the RF field. This non-conductive tip acts as a shrink-limiting mandrel to prevent the veins from shrinkage to a diameter less than the catheter tip and can extend 2 to 25 mm past the electrode 14. Both electrodes 14 and 16 are preferably made from stainless steel. An insulator material 18 is located between the end electrode and the ring electrode. The catheter 10 and electrodes 12 should be constructed from materials which would allow visualization under fluoroscopy x-ray, ultrasound, or other imaging techniques. For example, the catheter 10 can be configured to deliver x-ray contrast medium to allow visualization by fluoroscopy. Contrast media injected into the vein can be used to assess the condition of the vein and the relationship of the catheter to the treatment area of the vein by phlebography during the shrinkage process.

The catheter 10 includes a stranded, twisted center conductor 20 surrounded by a layer of insulation 22 which is preferably formed from TFE Teflon®. A silver-coated copper braid 24 surrounds the insulated center conductor, and provides flexible and torqueable characteristics to the catheter shaft. A sheath 26 covers the copper braid 24. The sheath 26 is preferably made of an electrically resistive, biocompatible material with a low coefficient of friction such as Teflon®. The center conductor 20 is connected to a power source 34 such as an RF generator, to provide RF energy to the electrodes 12.

While the electrodes 12 have been described as ring electrodes, other electrode configurations and arrangements can be used. For example, equidistantly spaced longitudinal electrodes can be used to provide omnidirectional and circumferential shrinkage and to minimize lengthwise contraction of the vein. The electrodes form an RF field circumferentially around the electrode.

It is to be understood that although a bipolar arrangement is described, a monopolar arrangement may also be used. In a monopolar arrangement, an inside electrode, such as a mesh or wire electrode, is inserted into a cavity in a patient's body. An outer electrode having a much larger surface area than the inside electrode is placed on the outer surface of the patient's body near the treatment site. For example, an external metal plate is placed on the skin over the region to be treated by the inside electrode. The electrodes are connected to a RF generator which produces an electric field within the patient's body. Because the surface area of the inner electrode is much smaller than that of the outer electrode, the density of the electric field is much higher around the inside electrode. The electric field reaches its highest density between the two electrodes in the region near the inside electrode. The increased density of the field around the inside electrode allows localized heating of the tissues surrounding the inside electrode. The degree of heating may be dependent on such factors as the impedance and dielectric constant of the tissue being heated.

The end ring electrode 14 and the ring electrode 16 are preferably located between the sensors 30 for measuring values such as impedance. In measuring impedance, as will be described in further detail later, the area between the electrodes often provides the most relevant data. It is to be understood that the sensors 30 may be used to measure other values including temperature and ultrasound signals. Further, the positioning of the sensors 30 on the catheter 10 can vary depending on the value being measured. For example, when measuring temperature, it may be desirable to place the sensor on or immediately adjacent to the electrode. The temperature sensor can sense the temperature of the tissue around the electrodes. When measuring echo signals of pulsed ultrasound, the sensors may be placed between the electrodes, or at the tip of the catheter. When measuring pulse echo ultrasound signals, the catheter is preferably rotated to resolve an image of the environment surrounding the catheter and the sensors.

The sensors 30 measure parameters which can be used to determine the extent of vein shrinkage. For example, the sensors 30 can be sensing electrodes which measure the impedance of the venous tissue in contact between the end electrode 14 and the ring electrode 16. A constant RF current is emitted from the active end electrode 14 to the return ring electrode 16. Also, the impedance may be measured between the electrodes 14 and 16 directly. The voltage across the electrodes is measured by the sensing electrodes to detect the impedance of the volume between the electrodes. The voltage measured is proportional to the impedance Z between the electrodes, where $Z=V/I$ and the current, I, is constant. The impedance changes as a function of the diameter of the vein because there is less blood and less conductance as the venous diameter decreases. As the volume decreases due to shrinkage, the amount of conductive volume between the electrodes decreases, and the increased impedance causes a corresponding increase in the measured voltage. This technique allows for the measurement of vein shrinkage in relative terms. The signals from the sensing electrodes can be input to a monitor, or microprocessor 32 which could send control signals to the RF generator 34 in order to control the application of RF energy to the electrodes in accordance with the relative impedance measured. Alternatively, the signals from the sensing electrodes can be displayed visually on a monitor in order to allow for manual control by the physician.

In an alternate embodiment, the sensors 30 can instead be temperature sensors such as thermistors. The temperature sensors may be included on the catheter near the electrodes on the working end to monitor the temperature surrounding the electrodes and the venous section being treated. Application of RF energy from the electrodes may be halted when the monitored temperature reaches or exceeds the specific temperature at which venous tissue begins to shrink. The signals from the temperature sensors can be input to the microprocessor 32 for controlling the application of RF energy to the electrodes in accordance with the monitored temperature.

Instead of sensing electrodes or thermistors, another embodiment includes ultrasonic piezoelectric elements which emit pulsed ultrasound waves as the sensors 30. The piezoelectric elements are operated in a pulse-echo manner to measure the distance to the vein wall from the catheter shaft. Again, the signals representative of the pulse-echo would be input to the microprocessor 32, or to a monitor to allow for manual control, and the application of RF energy would be controlled in accordance with the distance computed between the catheter and the vein wall.

Figure 8:
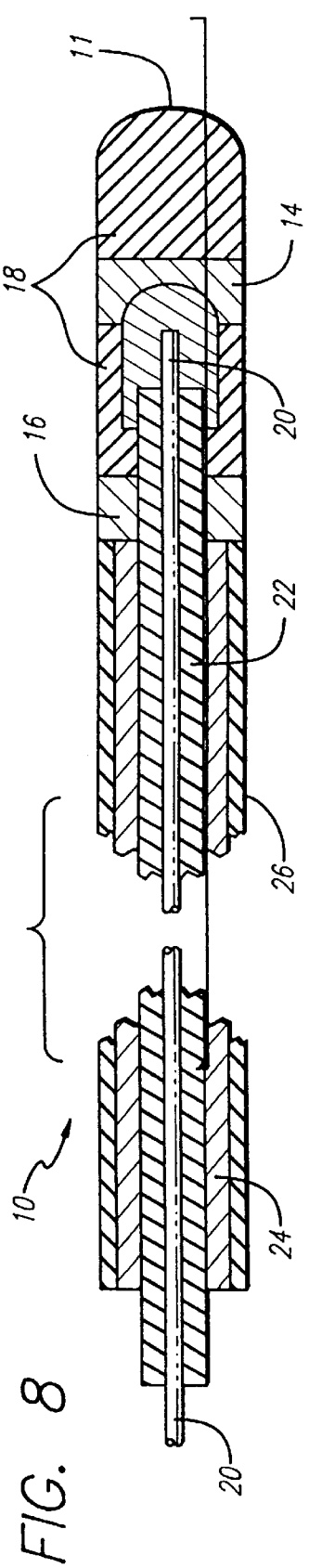
FIG. 8 shows a partial cross-sectional view of an embodiment of the catheter having a flush tip at the working end and ring electrodes for treating a dilated vein in accordance with the present invention.

The working end 11 of the catheter 10, as shown in FIG. 7, is rounded to provide an atraumatic tip which minimizes any incidental damage as the catheter is manipulated within the vein. The working end 11 of the catheter 10 can have an enlarged dimension which limits the amount of local vein shrinkage. An enlarged atraumatic tip may be achieved using a bulbous shape for the working end 11. Different sized working ends 11 and electrodes 12 can be manufactured separately from the catheter 10 for later assembly with the shaft of the catheter 10 so that a single catheter shaft may be used with working ends having a variety of diameters. A working end having a specific size or shape could then be used with the catheter 10 depending on the type of vein being treated. For example, certain larger veins have a diameter of seven to eight millimeters (mm), while other veins only have a diameter of 2 to 3.5 mm. Alternatively, the working end 11 and the ring electrodes 14 and 16 can be flush with the shaft of the catheter as shown in FIG. 8. Other methods, such as monitoring the amount of shrinkage by fluoroscopy, may be used to determine and control the amount of shrinkage. In other respects, the construction of the catheter in FIG. 8 is similar to that of FIG. 7, as previously discussed.

Figure 9:
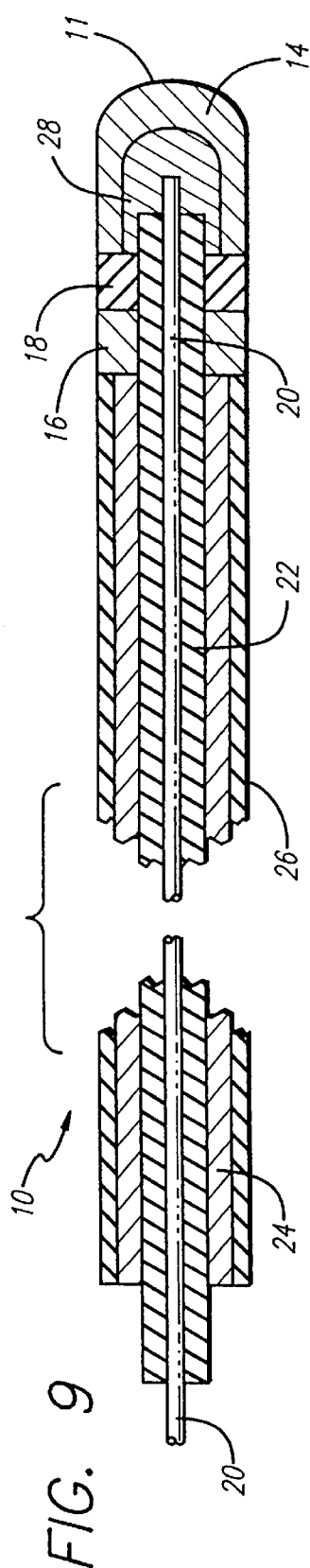
FIG. 9 shows a partial cross-sectional view of an embodiment of the catheter having a cap electrode for treating a dilated vein in accordance with the present invention.

Another embodiment of the catheter 10 includes an end electrode 14 which is a cap electrode formed on the tip of the working end 11 of the catheter 10. As shown in FIG. 9, the end electrode 14 is preferably fabricated from stainless steel. The end electrode 14 acts as the active electrode, and the ring electrode 16 acts as the return electrode. The cap electrode 14 of the catheter 10 is rounded to provide an atraumatic tip so as to minimize any damage to the surrounding venous tissue as the catheter is manipulated through the vein. The outer diameters (O.D.) of the electrodes 14 and 16 in one example size is 7 French or about 2.3 mm. Alternatively, the cap electrode and the working end 11 of the catheter 10 may have an enlarged dimension from the remainder of the catheter. The electrodes and the working end, as shown in the exemplary FIG. 9, are substantially flush with the remainder of the catheter. The braid sheath 26 covers the silver-coated, copper braid 24 of the catheter, and the sheath is flush with the outer diameter of the ring electrode 16. An insulator tube 18 is located between the end electrode and the ring electrode. At the working end of the catheter, a solder fill 28 is formed between the center conductor 20 and the end electrode 14. The center conductor 20 is isolated from the ring electrode 16 by insulation 22. The end cap electrode of FIG. 9 does not limit shrinkage of the vein adjacent to the tip of the catheter and therefore can allow the vein to shrink completely if desired.

Figure 10:
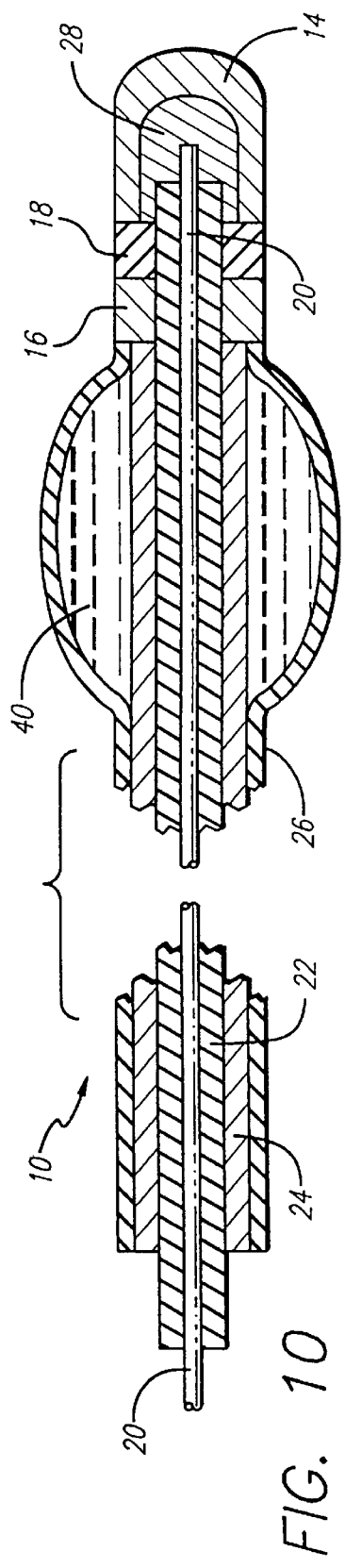
FIG. 10 shows a partial cross-sectional view of another embodiment of the catheter having a cap electrode and a balloon to center the placement of the electrode within the vein to be treated.

In another embodiment, an inflatable balloon 40 coaxially placed over the braided shaft can center the catheter 10 and the electrodes 14 and 16 within the vein lumen in order to avoid unintended electrode contact with the vein lumen which could otherwise result in uneven heating of portions of the vein lumen. As shown in FIG. 10, the balloon 40 is located adjacent to the electrode 16 which is closer to the connecting end of the catheter. The balloon 40 is preferably expandable and compliant, and fabricated from an elastic material such as latex, which can provide intermediate diameters. The balloon can be inflated with saline or other conductive solutions.

As discussed in connection with FIG. 6, it can be desirable to maintain selective apposition between the electrodes and the venous tissue at the treatment site. An embodiment of the catheter 10, shown in FIGS. 11a, 11b and 11c, is capable of being deflected by a shaft deflection wire 29. The catheter includes a silver-coated copper shield 24 and an outer layer of insulation 26. The electrodes 12 can be four circumferentially spaced longitudinal electrodes, as previously discussed. FIGS. 11a and 11c only show two of four longitudinal electrodes. The catheter 10 further includes a stiffening jacket 25 formed around the catheter shaft, except for the working end of the catheter. A central hollow wire lumen 27 extends through the length of the catheter. The shaft deflection wire 29 has a stiff bend formed near its working end, and is pushed through the wire lumen 27 of the catheter. The end of the wire 29 after the stiff bend which advances through to the tip of the working end of the catheter is preferably flexible and pliant. The stiffening jacket 25 prevents the catheter shaft from being deflected by the shaft deflection wire 29 until the deflection wire reaches the working end of the catheter. The bend in the deflection wire 29 moves the working end 11 of the catheter to one side. The electrodes 12 can then be selectively placed in apposition with the specific venous tissue to be treated. A contrast medium can also be administered to the treatment site through the lumen 27. Further, a cooling solution or fluid may be delivered to the treatment site through the lumen 27. Side ports 30 for the lumen can be formed at the working end near the electrodes 12 for delivering the contrast medium and the cooling fluid. Alternatively, the lumen 27 could be closed at the tip of the working end of the catheter in order to allow an injection of contrast media or cooling solution to be forced out the side ports 30. Closing the lumen 27 at the tip further allows the deflection wire 29 to be made more stiff without concern for the stiffer wire extending past the catheter.

Another embodiment uses an asymmetrical balloon 40 to deflect the electrodes 12 at the working end 11 of the catheter to one side. The electrodes 12 are a pair of longitudinal electrodes located on one side of the catheter. As shown in FIGS. 12a and 12b, the balloon 40 is located on the opposite side of the catheter. When the balloon 40 is inflated, the opposite side of the working end 11 accommodating the longitudinal electrodes is moved into apposition with the venous tissue to be treated. After treating the dilated venous section, the balloon 40 can be deflated, and the catheter removed from the vasculature. It should be noted that the other mechanisms for deflecting the working end of the catheter may be used. For example, a bendable actuation wire may be used on one side of the catheter in order to perform a function similar to that of the asymmetrical balloon. The catheter further includes the jacket 26, the braid 24, and the TFE insulation 22, and is similar in construction to the previously discussed embodiments.

In another embodiment, as shown in FIG. 13, the catheter 10 includes bowable electrodes 12 in the form of four conductive elongate members. The bowable electrodes 12 are similar to longitudinal electrodes formed along the circumference of the catheter, but are not fixed to the catheter. The catheter itself can fit through a suitably sized sheath for the procedure. For example, a 9 French sheath, which has about a 3 mm diameter, may be used. The working end 11 of the catheter includes a movable tip 31 manually controlled by a diameter actuator 33 located at the connecting end of the catheter. The movable tip 31 is connected to the diameter actuator 33 by a central wire (not shown) running through the catheter. The diameter actuator 33 may be threaded onto the connecting end of the catheter. Maneuvering the actuator 33 into and out of the connecting end of the catheter causes a corresponding movement in the movable tip 31 at the working end of the catheter. If the movable tip 31 is pulled toward the connecting end by the diameter actuator 33, then the electrodes 12 are bowed outwardly. The bowable electrodes 12 preferably expand out to treat veins up to 8 mm. If the movable tip 31 is pushed out by the diameter actuator 33, the bowable electrodes 12 are then retracted towards the shaft of the catheter. Consistent contact of the electrode can be maintained with the vein wall.

The extent of shrinkage can be controlled by the effective diameter of the catheter and the electrode combination. The electrodes 12 may be bowed radially outwards as part of the effective diameter of the catheter so as to come into apposition with the vein wall. As RF energy is applied, the vein begins to shrink down to the effective diameter of the catheter. The effective diameter of the catheter is reduced under the control of the physician to control the amount of shrinkage. As the effective diameter is decreased, the electrodes continue to maintain apposition with the venous tissue. As before, the extent of vein shrinkage can be monitored by fluoroscopy, or any other suitable method. After shrinking the vein to the desired diameter, the application of RF energy from the electrodes 12 is ceased. The desired diameter can be the final effective diameter of the catheter, as defined by the deflected electrodes 12.

The electrodes 12 may be fabricated from spring steel or nitinol so that the electrodes 12 would be biased to return to a reduced diameter profile. Where the entire length of the bowable longitudinal electrode is conductive, insulation 35 may be provided over the majority of the electrode surface in order to prevent any unintended heating effects. The ends of the electrodes are insulated from each other to prevent creating variable field densities at the ends, especially as the effective diameter increases which would create even greater field disparities between the ends and the bowed midsection. The insulation 35 can be polyimide or another type of insulating film. Insulation 35 provided along the back of the electrodes away from the vein wall further prevents heating of the blood flowing in the vein, which should also reduce the likelihood of coagulation. The remaining exposed area of the electrode is preferably the area which contacts the vein wall during apposition. The heating effect is then focused along the vein wall. The exposed surface area of the electrode should be as great as allowable while maintaining a consistent distance between the exposed sections of the electrode along the circumference of the effective diameter. The larger the exposed surface of the electrodes apposed against the vein wall during shrinkage, the greater the surface area of the vein wall affected by the electric field generated by the electrodes.

Another embodiment of the catheter 10, as shown in FIG. 14, includes bowable elongate members 32 having one end anchored to the working end 11 of the catheter, and the other end slidably connected to the catheter towards the connecting end. The catheter shown in FIG. 14 is similar to that shown in FIG. 13, except that instead of having the elongate members act as the electrodes themselves, the electrodes 12 are located on the elongate members 32. The elongate members 32 preferably include a flat central area 34 for the electrodes 12. The central area 34 remains substantially flat as the elongate members 32 are deflected and bowed outwardly. The substantially flat central area allows for a more uniform contact with the vein wall. The flat area establishes a larger surface area to assure contact between the electrode 12 on the elongate member and the vein wall. It is to be understood that the flat area 34 need not be centrally located on the elongate member 32. The flat area should be located so as to be the first area that contacts the vein wall. The elongate members 32 shown in FIG. 14 are connected to a sliding sleeve 36 formed along the exterior of the catheter shaft. As the electrodes 12 are moved radially outwards and inwards, the slidable sleeve 36 is moved towards and away from the working end.

The balloon 40 can be furnished between the catheter shaft, and the elongate members 32. Manual manipulation of the sliding sleeve is not required in this embodiment, and the sleeve need not travel any substantial length of the catheter. The balloon 40 is inflated and comes into contact with the elongate members 32. As the balloon 40 is further inflated, the electrodes 12 are moved outwardly in a radial direction as the elongate members are deflected and bowed by the expanding balloon 40. The balloon is preferably inflated using a non-conductive fluid, especially where the elongate members contain the electrodes, or where the elongate member itself is conductive so as to act as the electrode. When the proper diameter for the electrodes is reached, the inflation of the balloon ceases, and the application of the RF energy begins. The balloon 40 covers a greater surface area over the venous treatment site, and ensures proper electrode placement relative to the vein wall while controlling the amount of venous shrinkage. More precise control over the shape and diameter of the balloon can also be possible using the bowable members. As RF energy is applied, the vein begins to shrink down to the effective diameter of the catheter. The effective diameter of the catheter is reduced under the control of the physician to control the amount of shrinkage. As the effective diameter is decreased, the electrodes continue to maintain apposition with the venous tissue. The application of RF energy from the electrodes 12 is terminated after shrinking the vein to the desired diameter, which is the final effective diameter as defined by the diameter of the balloon 40 and the deflected elongate members 32. The balloon 40 is then is deflated to a minimal profile. The elongate members 32 are preferably fabricated from spring steel or nitinol so that the elongate members 32 would be biased to return to a reduced diameter profile when the balloon is deflated.

A cross-sectional view of the electrodes 12 of FIG. 14 along lines 15—15 is shown in FIG. 15a. In the four-electrode configuration, a preferred embodiment is to have the electrodes 12 spaced equidistantly apart along the circumference of the catheter. The polarity of each electrode is preferably opposite to the polarity of the immediately adjacent electrodes. Thus, a uniform RF field would be created along the circumference of the catheter by the alternating electrodes. In another embodiment, as shown in FIG. 15b, if adjacent electrodes were to be moved closer together, two effective pairs of active electrodes of opposite polarity would be formed along the circumference of the catheter. While an RF field would still be formed along the entire circumference of the catheter, the RF field would be strongest between the closest adjacent electrodes of opposite polarity. Shrinkage of the vein would be concentrated where the RF field was strongest.

In an alternative embodiment of that discussed in connection with FIG. 14, the outer sleeve 36 can extend down the length of the catheter to allow the operator or physician to mechanically control the effective electrode diameter during the application of RF energy, so that a separate balloon 40 is not required. Moving the slidable sleeve toward the working end 11 of the catheter causes the electrodes to deflect and radially bow outward to an increased diameter. The outer sleeve 34 can be moved a preset distance to cause the electrodes to bow outwardly to a known diameter. Bowing the electrodes outwardly also places the electrodes in apposition with the venous tissue to be treated. Moving the sleeve 34 toward the connecting end of the catheter pulls back and flattens the electrodes against the catheter before insertion or withdrawal from the vein. Moving the sleeve controls the diameter of the electrode deployment for proper treatment of vein lumen having different diameters, and for providing varying degrees of vein shrinkage. For example, the electrodes could be placed in contact with the venous tissue, and the effective diameter could be mechanically reduced to control shrinkage while RF energy was being applied.

In another embodiment, instead of an outer sleeve, the ends of the elongate members that would otherwise be attached to the outer sleeve are instead slidably located within longitudinal slots or channels disposed along the circumference of the catheter. The ends of the bowable members would slide towards the working end within these channels as the members are deflected or bowed outwardly, and retreat back towards the connecting end in order to return to their original configuration.

In another alternate embodiment, the electrodes and the elongate members could be replaced by a single wire mesh or braided electrode, preferably when applying RF energy in a monopolar configuration. As before, the balloon could radially extend the mesh electrode outward into apposition with the vein wall. The balloon can also control the amount of vein shrinkage.

An alternative method for changing the effective diameter of the catheters in FIGS. 13 and 14 is to move the electrodes 12 into direct contact with the vein wall. As the electrodes emit RF energy, the vein wall shrinks and pushes the electrodes inwardly towards the catheter. The vein shrinkage reduces the effective diameter directly, rather than by the active control of the physician, thereby eliminating the need for constant fine mechanical adjustments to the effective diameter. A mechanism such as a push rod or fixed-diameter balloon can be included to prevent further radial contraction of the electrodes at a specific effective diameter, thereby controlling and limiting the amount of vein shrinkage. This has the advantage of maintaining the electrodes in apposition with the venous tissue so that the tissue is heated more than the surrounding blood, without requiring the physician to constantly adjust the effective diameter of the catheter while applying the RF energy.

Other devices which are controllably expandable or extendable can be used to limit the shrinkage of the vein to a desired size. For example, mandrels can be advanced out through the sides of the catheter to define a diameter limit for shrinking the venous section. As another example, a bowable conductive deflection wire can be located on one side of the catheter for achieving apposition with the vein wall. Furthermore, even the non-expandable catheter shaft and electrode shown in FIG. 7 can be used to limit the amount of vein shrinkage during the procedure. The vein would merely shrink down to the fixed diameter of the catheter.

Other methods may be used with the catheter for maintaining apposition. For example, a pressure cuff may be used to apply external pressure to the leg to compress the treatment area so that the vein wall comes into contact with the electrodes. Apposition of the electrodes with the venous tissue would be maintained by the applied external pressure. Such external compression may be used when treating the superficial veins. Methods other than the aforementioned mechanical methods may also be used to control the magnitude of vein shrinkage. Such non-mechanical methods include controlling the time and temperature of the venous RF treatment.

The working end of the catheter 10 could be constructed to have a bend near the working end as shown in FIG. 11 so that the catheter can be rotated to create a stirring effect within the vein in order to achieve more uniform heating of the venous tissue for more even shrinkage. Rather than a permanent bend, the catheter can be manufactured to provide a controllable bend near the working end. For example, the bend may be formed from a shape-memory metal, manipulatable by a system of wires, a torquable braid, or a permanent bend in the catheter.

Another method for controlling the heat transfer to achieve more uniform heating is by using an external tourniquet to reduce blood flow or compress the vein around the catheter at the venous treatment site. By reducing blood flow either by external compression or an intravenously inflated occlusive balloon, the influence of blood flow through the vein, which can carry heat away from the treatment site, is minimized. The heat transfer to the venous tissue during the procedure is less impacted by the blood flow, and the shrinkage rate of the vein would therefore be more predictable. Sufficient pressure may also be established by the external tourniquet to cause the vein to come into apposition with the electrodes.

Figure 16:
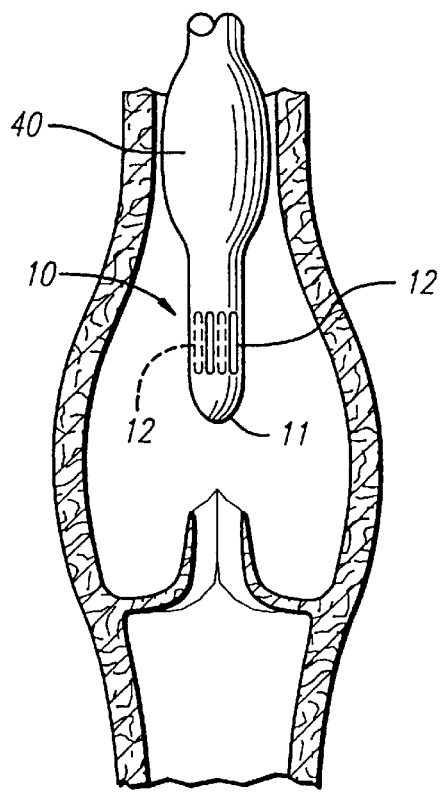
FIG. 16 shows a partial cross-sectional view of another embodiment of the catheter having four equidistantly spaced electrodes, and being delivered retrograde to a venous treatment site in accordance with the present invention.

In another embodiment, as shown in FIG. 16, an occlusive centering balloon 40 is used to retain a static pool of blood near the venous treatment site. A single occlusive balloon 40 may be used in conjunction with the venous valve to retain a pool of blood to be heated, wherein the electrodes 12 are located between the venous valve and the occlusive balloon 40. Two occlusive balloons (not shown) may be formed on either end of the electrodes to create a static pool of blood at a venous treatment site away from the venous valve. Such an arrangement isolates and protects the venous valve when treatment of the valve is not desired. The occlusive balloons may also be used to center the electrode within the vein lumen.

Although not limited to the occlusive balloon embodiment shown in FIG. 16, the catheter 10 further includes the electrodes 12 arranged in longitudinal fashion around the circumference of the catheter. This embodiment is similar to the embodiments disclosed and described in connection with the FIGS. 13 and 14, however, the electrodes in this instance are fixed on the catheter and do not bow outwards. This fixed diameter arrangement allows a RF field to be formed along the circumference of the catheter. Such an arrangement can provide omnidirectional shrinkage and avoid lengthwise contraction of the vein. The particular positioning and orientation of the longitudinal electrodes is preferably as shown in FIG. 15a.

A balloon expandable embodiment, as shown in FIG. 17, includes the four longitudinal electrodes 12 arranged in longitudinal fashion around the circumference of the balloon 40 of the catheter 10. This embodiment is similar to the embodiments disclosed and described in connection with FIGS. 13 and 14, so as to provide omnidirectional shrinkage and minimize lengthwise contraction of the vein. The particular positioning and orientation of the longitudinal electrodes is preferably equidistant as shown in FIG. 15a. The catheter 10 as shown in FIG. 17 is an over-the-wire type in which the catheter travels over a guide wire 42 through a guidewire lumen 52. The catheter 10 further includes the braided shield 24 surrounding the guidewire lumen 52. A braid tube 54 is formed around the braid 24. The lumen 56 for the balloon 40, and the balloon tube 55, encircle the braid tube 54. The braid tube forms a sealing barrier against the inflation fluid leaking into the guidewire lumen 52 from the balloon lumen. The exterior of the catheter includes a retainer tube 57 holding the conductor leads 20, which connect the electrodes 12 to an RF generator. A cross-section of the shaft of the catheter 10 along lines 18—18 of FIG. 17 is shown in FIG. 18.

In another embodiment, the electrodes 12 are located under the balloon 40 of the catheter 10. This embodiment, which is shown in FIG. 19 and which is similar to that shown in FIGS. 17 and 18, allows for conductive heating of the venous tissue. The catheter 10 shown in FIG. 19 is an over-the-wire type in which the catheter travels over the previously introduced guide wire 42. The balloon is inflated and expands to come into contact with the venous tissue. As discussed previously, the inflated balloon 40 can be used to control or limit the magnitude of shrinkage of the vein to the outer diameter of the inflated balloon 40. The effective diameter can be controlled by the selective inflation and deflation of the balloon 40. The inflation medium of the balloon 40 is preferably a conductive fluid, such as saline solution, so that a significant amount of the RF energy will still be transferred to the surrounding venous tissue. However, the inflation medium may absorb a certain amount of the RF energy, which will then be converted to heat. This diffusion of the RF energy could provide greater control over the shrinkage of the vein. Alternatively, a conventional heater coil or curie point element could be used in place of the electrodes 12 in order to directly heat the inflation medium, which in turn would conductively transfer the heat to the venous tissue.

Figure 20:
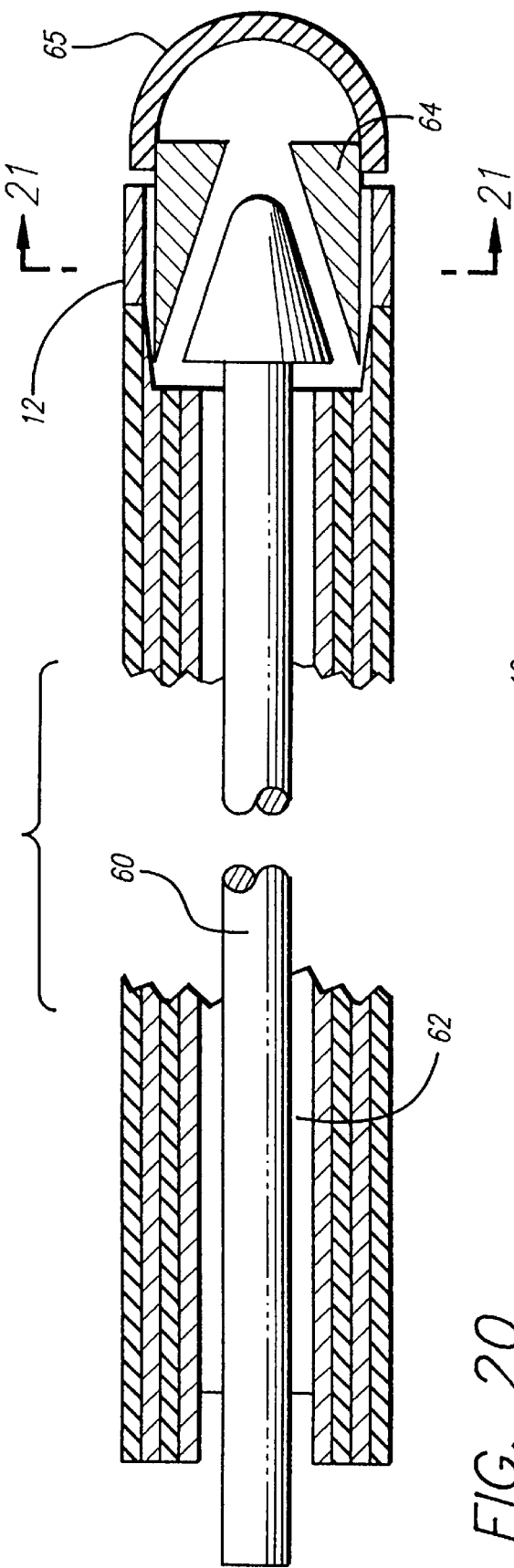
FIG. 20 shows a lengthwise cross-sectional view of another embodiment of the catheter having a conical wedge member for moving the electrodes at the working end of the catheter into apposition with the venous tissue in accordance with the present invention.
Figure 21:
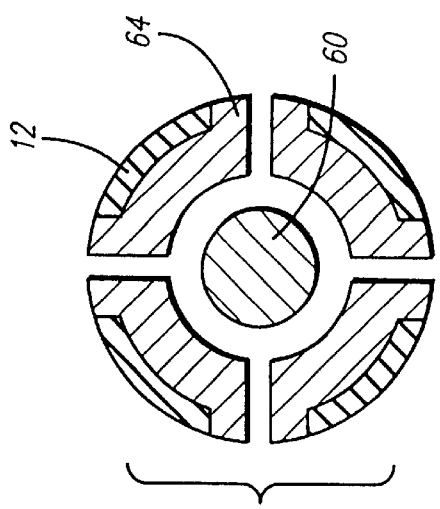
FIG. 21 shows a cross-sectional view taken along lines 21—21 in FIG. 20 in accordance with the present invention.

Another embodiment for controlling the effective diameter as shown in FIG. 20 involves using a central cone-shaped wedge actuator 60 within a central lumen 62 in the catheter. The electrodes 12 are flexibly mounted to the catheter at the working end. The wedge actuator 60 can be pushed forward to engage the complementary wedges holding the electrodes in order to increase the effective diameter of the electrode catheter at the working end. A cross-sectional view taken across lines 21—21 in FIG. 20 is shown in FIG. 21. Although the wedge actuator 60 is shown having a conical configuration, it is to be understood that any suitable shape may be used. For example, the circular cross-sections of a cone could be replaced by rectangular cross-sections to form a pyramid shape. In any event, as the larger diameter sections of the wedge actuator 60 engage the complementary wedges 64 within the working end of the catheter, the electrodes 12 are forced radially outward into apposition with the venous tissue. The tip 65 of the working end of the catheter is preferably flexible so as to accommodate the expanded diameter of the working end created by the wedge actuator and complementary wedges. The tip 65 is also composed of an biologically inert and electrically non-conductive material so as to prevent shrinkage past the catheter.

As can be readily ascertained from the disclosure herein, the procedure of the present invention is accomplished without the need for prolonged hospitalization or postoperative recovery. The curative restoration of venous function is possible without the need for continued lifestyle changes, such as frequent leg elevation, the wearing of relatively uncomfortable elastic support stockings or prolonged treatment of recurrent venous stasis ulcers. Moreover, the need for surgery of the arm and leg for transplantation of arm veins into the leg would not be necessary.

Early treatment of venous disease could prevent more serious complications such as ulceration, thrombophlebitis and thromboembolism. The cost of treatment and complications due to venous disease would be significantly reduced. There would be no need for extensive hospitalization for this procedure, and the need for subsequent treatment and hospitalization would also be reduced from what is currently needed. Furthermore, the minimally invasive nature of the disclosed methods would allow the medical practitioner to repair or treat several venous sections in a single procedure in a relatively short period of time.

It is to be understood that the type and dimensions of the catheter and electrodes may be selected according to the size of the vein to be treated. Although the present invention has been described as treating venous insufficiency of the lower limb such as varicose veins in the leg, the present invention may be used to intraluminally treat venous insufficiency in other areas of the body. For example, hemorrhoids may be characterized as outpocketed varicose veins in the anal region. Traditional treatments include invasive surgery, elastic ring ligation, and the application of topical ointments. Shrinking the dilated veins using RF energy can be accomplished in accordance with the present invention. Specifically, the catheter and electrode combination is introduced into the venous system, into the external iliac vein, the internal iliac vein, then either the hemorrhoidal or the pudendal vein. The catheter then delivers the electrode to the site of the dilated hemorrhoidal vein by this transvenous approach. Fluoroscopic techniques or any other suitable technique such as pulse-echo ultrasound, as previously discussed, can be used to properly position the electrode at the venous treatment site. The treatment site is preferably selected to be at least two centimeters above the dentate line to minimize pain. The electrode applies RF energy at a suitable frequency to minimized coagulation for a sufficient amount of time to shrink, stiffen, and fixate the vein, yet maintain venous function or valvular competency. This intraluminal approach avoids the risks and morbidity associated with more invasive surgical techniques such as hemorrhoidectomy, while significantly reducing reflux of blood in the area without necrosing or removing the venous tissue.

Another area of venous insufficiency relates to erectile impotency of the penis. A significant number of all physically-induced cases of impotence result from excessive drainage of blood from the penile venous system. Venous-drainage-impotence can be treated using the present invention. Catheters having a sufficiently small diameter can be used to deliver the electrodes through the dorsal vein of the penile venous system to shrink this venous outflow path. Fluoroscopic or ultrasound techniques can be used to properly position the electrode within the incompetent vein. RF energy or other radiant energy is applied from the electrodes at a suitable frequency to shrink the surrounding venous tissue in order to reduce the excessive amount of drainage from the penis while maintaining venous function or valvular competency. The amount of shrinkage of the vein can be limited by the diameter of the catheter itself, or the catheter or electrodes themselves can be expanded to the appropriate size. Ligation of these veins should be avoided so as to allow for the proper drainage of blood from an engorged penis which is necessary for proper penile function.

Another area of venous insufficiency suitable for treatment in accordance with the present invention involves esophageal varices. Varicose veins called esophageal varices can form in the venous system along the submucosa of the lower esophagus, and bleeding can occur from the swollen veins. Properly sized catheters can be used in accordance with the present invention to deliver the electrodes to the site of venous insufficiency along the esophageal varices. Endovascular access for the catheter is preferably provided through the superior mesenteric vein or portal vein to shrink the portal vein branches leading to the lower esophagus. Proper positioning of the electrode within the vein can be confirmed using fluoroscopic or ultrasound techniques. The electrodes apply RF energy or other radiant energy at a suitable frequency to shrink the vein and reduce the swelling and transmission of high portal venous pressure to the veins surrounding the esophagus while maintaining the function of the vein. The amount of shrinkage of the vein can be limited by the diameter of the catheter itself, or the catheter or electrodes themselves can be expanded to a predetermined diameter which limits shrinkage of the vein to that diameter.

While several particular forms of the invention have been illustrated and described, it will be apparent that various modifications can be made without departing from the spirit and scope of the invention. Accordingly, it is not intended that the invention be limited, except as by the appended claims.

What is claimed is:

1. An apparatus for applying energy to cause shrinkage of a vein, the apparatus comprising:

a catheter having a working end and an outer diameter, the outer diameter of the catheter is less than the inner diameter of the vein;

means for heating a venous treatment area to cause a reduction in the diameter of the vein, the means for heating is located at the working end of the catheter; and a plurality of bowable members having sufficient strength to limit the reduction in the diameter of the vein so that the vein remains patent for continued venous function.

2. The apparatus of claim 1, wherein the controlling means includes an inflatable balloon located at the working end of the catheter.

3. The apparatus of claim 1, wherein the plurality of bowable members move the heating means radially outwards from the catheter.

4. The apparatus of claim 1, wherein the bowable members include a portion capable of being bowed outwardly from the catheter.

5. The apparatus of claim 4, wherein the bowable member is conductive and the bowable conductive member further includes an insulating film covering the surface of the conductive member except for the portion bowed outwardly from the catheter and that contacts the vein wall, wherein the heating means includes the portion of the bowable conductive member.

6. The apparatus of claim 1, wherein the heating means is located on the bowable members.

7. The apparatus of claim 1, further comprising a sensor located at the working end of the catheter, wherein the controlling means includes a microprocessor receiving a signal from the sensor representing a condition at the treatment area.

8. The apparatus of claim 1, further comprising an impedance sensor located at the working end of the catheter, wherein the controlling means includes a microprocessor receiving a signal from the impedance sensor representing the impedance at the treatment area.

9. The apparatus of claim 1, further comprising a temperature sensor located at the working end of the catheter, and a microprocessor receiving a signal from the temperature sensor at the treatment area.

10. The apparatus of claim 1, wherein the heating means includes at least one electrode capable of emitting high frequency energy; the apparatus further comprising a microprocessor selecting a frequency for the electrode in order to minimize coagulation.

11. The apparatus of claim 1, wherein the heating means includes at least one electrode capable of emitting high frequency energy; the apparatus further comprising a microprocessor selecting a frequency for the electrodes in order to control the spread of the heating effect in the venous tissue.

12. The apparatus of claim 1, wherein the catheter includes a lumen for injecting a contrast medium into the hollow anatomical structure.

13. The apparatus of claim 1, wherein the catheter includes a lumen for injecting a cooling fluid for preventing thermal coagulation of blood in the vein.

14. The apparatus of claim 1, wherein the catheter includes a lumen for accepting a guidewire for navigating through the vein.

15. An apparatus for applying energy to cause shrinkage of a vein in order to restore valvular competency, the apparatus comprising:

a catheter having a working end and an outer diameter, the outer diameter of the catheter is less than the inner diameter of the vein;

means for heating a venous treatment area to cause shrinkage of the vein, the means for heating is located at the working end of the catheter; and means for controlling further shrinkage of the vein so venous valvular competency is restored, wherein the means for controlling shrinkage is located at the working end of the catheter and includes a bowable member having sufficient strength to limit reduction in the circumference of the vein.

16. The apparatus of claim 15, wherein the controlling means includes an inflatable balloon located at the working end of the catheter.

17. The apparatus of claim 15, wherein the controlling means includes a bowable member for moving the heating means radially outwards from the catheter.

18. The apparatus of claim 15, wherein the controlling means includes a bowable conductive member having a portion capable of being bowed outwardly from the catheter.

19. The apparatus of claim 15, wherein the bowable conductive member further includes an insulating film covering the surface of the conductive member except for the portion bowed outwardly from the catheter and toward the vein, wherein the heating means includes the portion of the bowable conductive member.

20. The apparatus of claim 15, wherein the controlling means includes the heating means.

21. The apparatus of claim 15, further comprising a sensor located at the working end of the catheter, wherein the controlling means includes a microprocessor receiving a signal from the sensor representing a condition at the treatment area.

22. The apparatus of claim 15, further comprising an impedance sensor located at the working end of the catheter, wherein the controlling means includes a microprocessor receiving a signal from the impedance sensor representing the impedance at the treatment area.

23. The apparatus of claim 15, further comprising a temperature sensor located at the working end of the catheter, wherein the controlling means includes a microprocessor receiving a signal from the temperature sensor at the treatment area.

24. The apparatus of claim 15, wherein the heating means includes at least one electrode capable of emitting high frequency energy; the apparatus further comprising a microprocessor selecting a frequency for the electrode in order to minimize coagulation.

25. The apparatus of claim 15, wherein the heating means includes at least one electrode capable of emitting high frequency energy; the apparatus further comprising a microprocessor selecting a frequency for the electrodes in order to control the spread of the heating effect in the venous tissue.

26. The apparatus of claim 15, wherein the catheter includes a lumen for injecting a contrast medium for determining the occurrence and extent of vein shrinkage.

27. The apparatus of claim 15, wherein the catheter includes a lumen for injecting a cooling fluid for preventing thermal coagulation of blood in the vein.

28. The apparatus of claim 15, wherein the catheter includes a lumen for accepting a guidewire for navigating through the vein.

* * * * *

UNITED STATES PATENT AND TRADEMARK OFFICE
CERTIFICATE OF CORRECTION

PATENT NO.     : 6,613,045 B1
DATED          : September 2, 2003
INVENTOR(S)    : Michael D. Laufer et al.

It is certified that error appears in the above-identified patent and that said Letters Patent is hereby corrected as shown below:

<u>Title page, Item [54] and Column 1, line 1,</u>
Delete "METHOD AND" from title.

Signed and Sealed this

Twenty-third Day of December, 2003

JAMES E. ROGAN
*Director of the United States Patent and Trademark Office*